United States Patent
Pasinetti

(10) Patent No.: US 8,921,347 B2
(45) Date of Patent: *Dec. 30, 2014

(54) COMPOSITIONS AND METHODS FOR TREATING ALZHEIMER'S DISEASE AND RELATED DISORDERS AND PROMOTING A HEALTHY NERVOUS SYSTEM

(75) Inventor: Giulio M. Pasinetti, New York, NY (US)

(73) Assignee: Icahn School of Medicine at Mount Sinai, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/486,439

(22) Filed: Jun. 1, 2012

(65) Prior Publication Data

US 2013/0123370 A1    May 16, 2013

Related U.S. Application Data

(63) Continuation of application No. 11/255,780, filed on Oct. 21, 2005, now Pat. No. 8,193,250.

(60) Provisional application No. 60/621,331, filed on Oct. 22, 2004.

(51) Int. Cl.
*A61K 31/075* (2006.01)
*A61K 31/045* (2006.01)

(52) U.S. Cl.
CPC ............. *A61K 31/075* (2013.01); *A61K 31/045* (2013.01)
USPC ...................................... 514/175

(58) Field of Classification Search
USPC ...................................... 514/715
See application file for complete search history.

(56) References Cited

U.S. PATENT DOCUMENTS

| | | | |
|---|---|---|---|
| 5,272,055 A | 12/1993 | Haley | |
| 5,550,166 A | 8/1996 | Ostlund et al. | |
| 6,486,127 B1 | 11/2002 | Gunn et al. | |
| 6,518,318 B1 | 2/2003 | Weeks | |
| 6,784,209 B1 | 8/2004 | Gardiner | |
| 2001/0041677 A1 | 11/2001 | Martin-Lomas et al. | |
| 2001/0053767 A1 | 12/2001 | Martin-Lomas et al. | |
| 2003/0232758 A1 | 12/2003 | St. George-Hyslop et al. | |
| 2004/0204387 A1 | 10/2004 | McLaurin | |
| 2004/0204564 A1 | 10/2004 | Rivier et al. | |
| 2006/0004096 A1 | 1/2006 | Larner | |
| 2006/0189582 A1 | 8/2006 | McLaurin | |
| 2006/0258754 A1 | 11/2006 | Larner et al. | |

OTHER PUBLICATIONS

Abraham et al., Alpha 1-antichymotrypsin is present together with the beta-protein in monkey brain amyloid deposits, Cell, 1998, 52:487-501.
Anson et al., Intermittent fasting dissociates beneficial effects of dietary restriction on glucose metabolism and neuronal resistance to injury from calorie intake, Proc. Natl. Acad. Sci. USA, 2003, 100:6216-6220.
Bates et al., Insulin-like effect of pinitol, Br. J. Pharmacol., 2000, 130:1944-1948.
Burns et al., Presenilin redistribution associated with aberrant cholesterol transport enhances beta-amyloid production in vivo, Neurosci., 2003, 23:5645-5649.
Cataldo et al., Lysosomal proteinase antigens are prominently localized within senile plaques of Alzheimer's disease: evidence for a neuronal origin, Brain Res., 1990, 513:181-192.
Cummings, Alzheimer's disease, N. Engl. J. Med., 2004, 315:56-67.
Davis et al., Effect of pinitol treatment on insulin action in subjects with insulin resistance, Diabetes Care, 2000, 23:1000-1005.
Gustafson et al., An 18-year follow-up of overweight and risk of Alzheimer disease, Arch. Intern. Med., 2003, 163:1524-1528.
Hendrie et al., Incidence of dementia and Alzheimer disease in 2 communities: Yoruba residingin Ibadan, Nigeria, and African Americans residing in Indianapolis, Indiana, JAMA, 2001; 285:739-747.
Ho et al., Diet-induced insulin resistance promotes amyloidosis in a transgenic mouse model of Alzheimer's disease, FASEB J., 2004, 18:902-904.
Holman and Kasuga, From receptor to transporter: insulin signaling to glucose transport, Diabetologia, 1997, 40:991-1003.
Hsiao et al., Correlative memory deficits, A-beta elevation, and amyloid plaques in transgenic mice, Science, 1996, 274:99-102.
Kawarabayashi et al., Age-dependent changes in brain, CSF, and plasma amyloid beta protein in the Tg2576 transgenic mouse model of Alzheimer's disease, J. Neurosci., 2001, 21:372-381.
King and Arendash, Behavioral characterization of the Tg2576 transgenic model of Alzheimer's disease through 19 months, Physiol. Behav., 2002, 15:627-642.
Kuusisto et al., Association between features of the insulin resistance syndrome and Alzheimer's disease independently of apolipoprotein E4 phenotype: cross sectional population based study, BMJ, 1997, 315:1045-1049.

(Continued)

*Primary Examiner* — San-Ming Hui
*Assistant Examiner* — Kathrien Cruz
(74) *Attorney, Agent, or Firm* — Fish & Richardson P.C.

(57) ABSTRACT

Methods of inhibiting the onset and progression of Alzheimer's disease (AD), mild cognitive impairment (MCI), and related neurodegenerative disorders involving amyloidosis are provided. The methods involve administering a composition comprising a therapeutically effective amount of D-pinitol to individuals who are at risk of developing the disease or have one or more symptoms of the disease. Also provided are methods of treating or preventing Alzheimer's disease or MCI that involve the use of such compositions. Also provided are methods of using D-pinitol to promote a healthy nervous system and as a food supplement.

7 Claims, 15 Drawing Sheets

(56) References Cited

OTHER PUBLICATIONS

Lammich et al., Constitutive and regulated alpha-secretase cleavage of Alzheimer's amyloid precursor protein by a disintegrin metalloprotease, Proc. Natl. Acad. Sci. USA, 1999, 96:3922-3927.

Larner et al., Isolation, structure, synthesis, and bioactivity of a novel putative insulin mediator. A galactosamine chiro-inositol pseudo-disaccharide Mn2+ chelate with insulin-like activity, J. Med. Chem., 2003, 46:3283-3291.

Lichtenthaler et al., Amyloid at the cutting edge: activation of alpha-secretase prevents amyloidogenesis in an Alzheimer disease mouse model, J. Clin. Invest., 2004, 113:1384-1387.

Luchsinger, Caloric intake and the risk of Alzheimer disease, Arch. Neurol., 2002, 59:1258-1263.

Mattson et al., Modification of brain aging and neurodegenerative disorders by genes, diet, and behavior, Physiol. Rev., 2002, 82:637-672.

Mattson, Pathways towards and away from Alzheimer's disease, Nature, 2004, 430:631-639.

McLaurin et al., Cyclohexanehexol inhibitors of Aβ aggregation prevent and reverse Alzheimer phenotype in a mouse model, Nature Medicine, Advance Online Publication, 2006, pp. 1-8.

McLaurin et al., Inositol Stereoisomers Stabilize an Oligomeric Aggregate of Alzheimer Amyloid β Peptide and Inhibit Aβ-induced Toxicity, Journal of Biological Chemistry, 2000, 275:18495-18502.

Meckling et al., Comparison of a low-fat diet to a low-carbohydrate diet on weight loss, body composition, and risk factors for diabetes and cardiovascular disease in free-living, overweight men and women, J. Clin. Endocrinol. Metab., 2004; 89:2717-2723.

Namba et al., Apolipoprotein E immunoreactivity in cerebral amyloid deposits and neurofibrillary tangles in Alzheimer's disease and kuru plaque amyloid in Creutzfeldt-Jakob disease, Brain Res., 1991, 541:163-166.

Ortmeyer et al., Chiroinositol deficiency and insulin resistance. II. Acute effects of D-chiroinositol administration in streptozotocin-diabetic rats, normal rats given a glucose load, and spontaneously insulin-resistant rhesus monkeys, Endocrinology, 1993, 132:646-65.

Phiel et al., GSK-3 alpha regulates production of Alzheimer's disease amyloid-beta peptides, Nature, 2003, 423:435-39.

Postina et al., A disintegrin-metalloproteinase prevents amyloid plaque formation and hippocampal defects in an Alzheimer disease mouse model, J. Clin. Invest., 2004, 113:1456-1464.

Qin et al., The PrP-like protein Doppel binds copper, J. Biol. Chem., 2002, 278:50970-50977.

Stern et al., The effects of low-carbohydrate versus conventional weight loss diets in severely obese adults: one-year follow-up of a randomized trial, Ann. Int. Med., 2004, 140:778-785.

Strittmatter et al., Binding of human apolipoprotein E to synthetic amyloid beta peptide: isoform-specific effects and implications for late-onset Alzheimer disease, Proc. Nat. Acad. Sci. USA, 1993, 90:8098-8102.

Vanhanen et al., Glucose intolerance, cognitive impairment and Alzheimer's disease, Curr. Opin. Neurol., 1998, 11:673-677.

Wang et al., Secretion of the beta/A4 amyloid precursor protein: Identification of a cleavage site in cultured mammalian cells, J. Biol. Chem., 1991, 226:16960-16864.

White, The insulin signaling system and the IRS proteins, Diabetologia, 1997, 40 Suppl. 2:S2-1.

Wisniewski and Frangione, Apolipoprotein E: a pathological chaperone protein in patients with cerebral and systemic amyloid, Neurosci. Lett., 1992, 135:235-238.

Yancy et al, A low-carbohydrate, ketogenic diet versus a low-fat diet to treat obesity and hyperlipidemia: a randomized, controlled trial, Ann. Int. Med., 2004, 140:769-777.

Figure 2
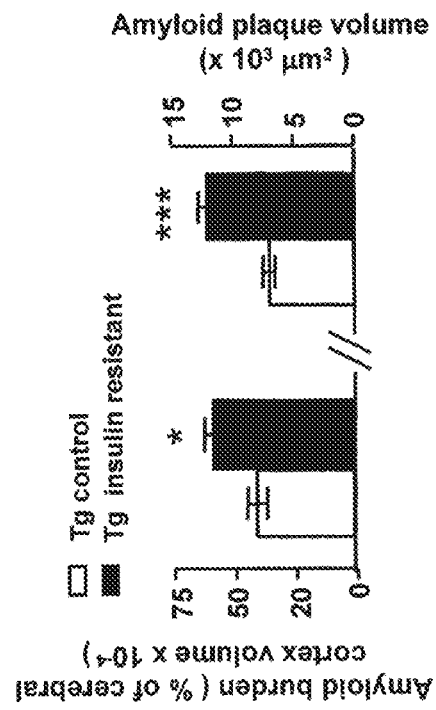
A Brain amyloid peptide contents
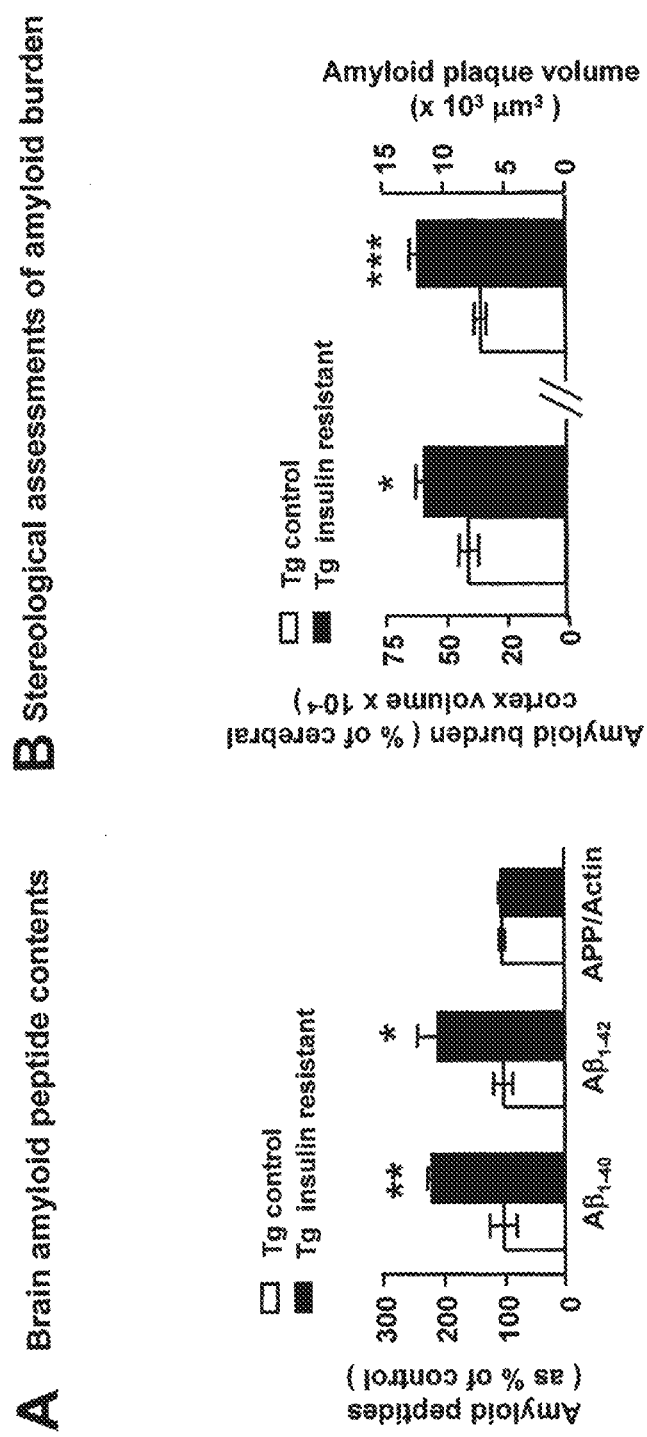
B Stereological assessments of amyloid burden

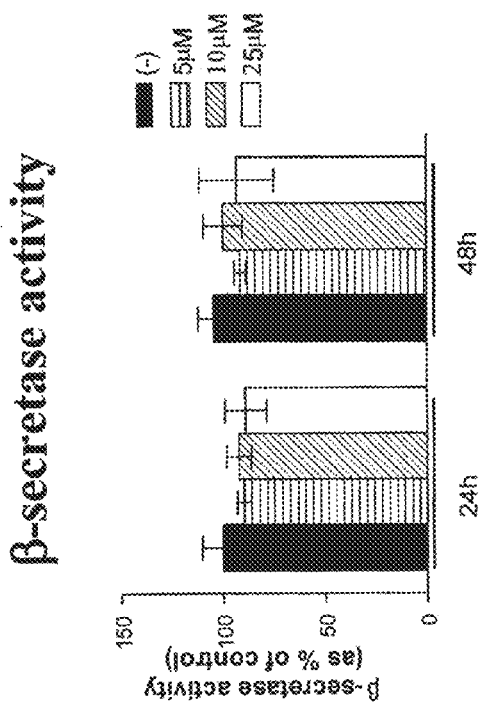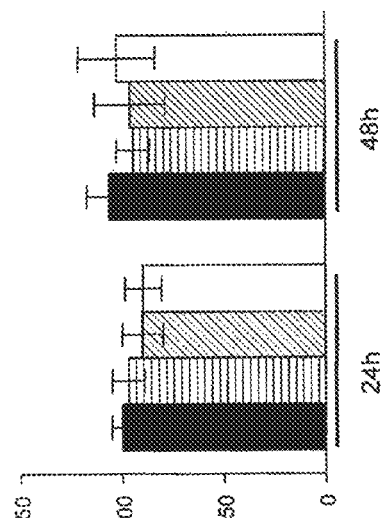
Figure 7

SEQUENCE LISTING

<160> NUMBER OF SEQ ID NOS: 1

<210> SEQ ID NO 1
<211> LENGTH: 42
<212> TYPE: PRT
<213> ORGANISM: Homo sapiens

<400> SEQUENCE: 1

Asp Ala Glu Phe Gly His Asp Ser Gly Phe Glu Val Arg His Gln Lys
1               5                   10                  15

Leu Val Phe Phe Ala Glu Asp Val Gly Ser Lys Lys Gly Ala Ile Ile
            20                  25                  30

Gly Leu Met Val Gly Gly Val Val Ile Ala
            35                  40

COMPOSITIONS AND METHODS FOR TREATING ALZHEIMER'S DISEASE AND RELATED DISORDERS AND PROMOTING A HEALTHY NERVOUS SYSTEM

This application is a continuation of application Ser. No. 11/255,780, filed Oct. 21, 2005, now U.S. Pat. No. 8,193,250, and claims priority to provisional application 60/621,331 filed on Oct. 22, 2004. Each of the aforementioned applications is hereby incorporated herein, by reference, in its entirety.

REFERENCE TO SEQUENCE LISTING

Pursuant to 37 C.F.R. 1.821(c), a sequence listing is submitted herewith as an ASCII compliant text file named "SEQUENCE_LISTING.txt" that was created on Jan. 21, 2013, and has a size of 838 bytes. The content of the aforementioned file named "SEQUENCE_LISTING.txt" is hereby incorporated by reference in its entirety.

FIELD OF THE INVENTION

The present invention relates generally to methods of inhibiting the onset and progression of Alzheimer's disease (AD), mild cognitive impairment (MCI), and related neurodegenerative disorders involving amyloidosis. The methods involve administering a composition comprising a therapeutically effective amount of D-pinitol to individuals who are at risk of developing the disease or have one or more symptoms of the disease. The invention also relates to methods for treating or preventing Alzheimer's disease or MCI that involve the use of such compositions. The invention further provides methods to promote the general health of the nervous system through administration of active ingredient compositions. The invention further provides methods to inhibit or treat AD or MCI in an individual based on reducing caloric intake by the individual. The invention further relates to animal and cellular systems for the study of AD, MCI, and related disorders, and the identification of reagents useful in treating amyloidosis.

BACKGROUND OF THE INVENTION

Dementia and the Prevalence of Alzheimer's Disease

Dementia is a neurodegenerative disorder that affects as many as 10% of individuals over 65 years of age, and more than 35% of those over 85 (Hofman et al. Int. J. Epidemiol. 1991; 20:736-748; Jorm and Jolley. Neurology 1998; 1:728-733; Lobo et al. Neurology 2000; 4Suppl5:S4-S9). Dementia is a complex syndrome and is typically progressive or chronic. The spectrum of this disorder is broad-sweeping and encompasses multiple cognitive functions, including learning, memory, thinking, calculation, language, judgment, comprehension, and spatial and temporal recognition. In addition, the syndrome can be preceded or accompanied by disruption in emotional states, including emotional control, social behavior, and motivation.

Of the diseases leading to dementia, Alzheimer's Disease (AD) is the most common, accounting for greater than half the cases in people over 65 years of age. First recognized nearly a century ago (Alzheimer. Algemeine Zeitschrift fur Pschiatrie. 1907; 64:146-148). Alzheimer's disease (AD) is a devastating disorder, affecting nearly 2-3 million individuals in the United States and about 15 million people world-wide (including all races and ethnic groups). Moreover, because advanced age in the biggest risk factor for AD, the prevalence of this disorder doubles every 5 years beyond age 65 (National Institute on Aging: Prevalence and costs of Alzheimer's disease. Progress Report on Alzheimer's Disease. NIH Publication No. 99, 3616, November 1998; Polyikoski et al. Neurology 2001; 56:1690-1696).

Pathology of Alzheimer's Disease

The pathological hallmarks of clinical AD are confined to the central nervous system (CNS) and comprise two principal features: amyloid deposits and neurofibrillary tangles (NFT). Amyloidosis—the deposition of amyloid—occurs through the vascular and neuronal architecture of the CNS.

Although amyloidosis occurs to a limited extent in probably all individuals, especially with advanced age, it is aberrantly high in AD and related disorders. The main molecular component of amyloid is β-amyloid, a highly hydrophobic peptide, derived from processing of the amyloid precursor protein (APP; See FIG. 6). This peptide aggregates into filaments in an anti-β-pleated sheet structure. Elevated expression disrupts the structure and function of neuronal and glial cells, ultimately resulting in extensive cell death in regions of the brain underlying higher cognitive functions, (Francis et al. J. Neurol. Neurosurg. Psychiatry 1999; 66:137-147).

These pathological hallmarks, however, reflect terminal points of a lengthy disease process. Consequently, post-mortem brain studies have yielded little insight into the molecular and biochemical components involved in the initiation and progression of this disease. Underscoring this issue is the molecular complexity of amyloid, which comprises many additional proteins, including α1-anti-chymotrypsin (Abraham et al. Cell 52:487-501, 1988), cathepsin D (Cataldo et al. Brain Res. 1990; 513:181-192) and apolipoprotein E (apoE) (Namba et al. Brain Res. 1991; 541:163-166; Wisniewski and Frangione. Neurosci. Lett. 1992; 135:235-238; Strittmatter et al. Proc. Nat. Acad. Sci. USA 1993; 90:1977-1981).

Etiology of Alzheimer's Disease

Although amyloidosis is a conserved feature of AD, the underlying etiology is highly complex and the vast majority of instances likely involves multiple genetic and environmental determinants. AD has been divided into two categories: Familial AD (FAD) and Sporadic AD. FAD is associated with mutations in least three known loci: presenilin 1 (PS1), presenilin 2 (PS2) and amyloid precursor protein (APP) genes. Studies of FAD have underscored the importance of amyloid β-peptide (Aβ) in AD, but are limited in scope: FAD only accounts for a small fraction of AD cases (less than 5%), has a much earlier age onset (often in the 40's) and follows clear patterns of inheritance (Bird et al. Ann. Neurol. 1989; 25:12-25; Heston and White. Behavior Genet. 1978; 8:315-331; Pericak-Vance et al. Exp. Neurol. 1988; 102:271-279).

In contrast Sporadic AD can reflect a genetic etiology, but it is not a tight linkage. The ε4 allele of the apoliprotein E locus, for example, increases the risk of developing AD; however, its presence does not guarantee AD, nor does its absence preclude it. (Consensus report of the Working Group. Neurobiology of Aging 1998; 19:109-116).

The vast majority of AD cases, therefore, will likely comprise a complex etiology, implicating multiple genetic and environmental factors. In light of such constraints, many investigations have focused on identifying biological markers that correlate with different stages of AD. Candidates for such markers have included cerebrospinal fluid profiles, peripheral tissue markers, pharmacologic and neuroendocrine probes, and behavioral and biochemical correlates. (See, e.g., Neurobiology of Aging 1998; 19:109-116 for a review).

Nevertheless, such biological markers are not likely to provide a cure-all for at least two reasons. First, the extended time course of AD poses the inescapable challenge of separating normal changes during aging, such as impairments of cognitive abilities, from pathogenic ones. Second, dietary, environmental, and genetic factors are not easily controlled with this approach, presenting the additional challenge of resolving diagnostic effects within a heterogeneous background. At present, AD remains incurable. Nor is there available a treatment that effectively prevents AD or reverses its symptoms.

Thus, there is a need in the art to develop new approaches to identify candidate compounds effective to inhibit and treat symptoms or clinical manifestations of AD and related disorders. The present invention meets this need by disclosing new mechanistic and temporal links between the induction of an insulin-resistant Type 2 diabetes state—a known risk factor for AD—and the subsequent appearance of cognitive defects and β-amyloid pathologies in the brain. In turn, these findings reveal specific and unexpected uses for D-pinitol— an insulin sensitizing compound—that include inhibiting AD pathology.

SUMMARY OF THE INVENTION

In one embodiment, the invention provides a method of inhibiting a symptom of Alzheimer's disease in an individual by administering a therapeutically effective amount of a composition comprising D-pinitol. In a further embodiment, the method provides a composition that is pharmaceutically acceptable. In another aspect, the method comprises administering the composition prior to the onset of Alzheimer's disease. In yet another aspect, the method comprises administering the composition to an individual who is asymptomatic and at risk of developing Alzheimer's disease, with or without NIDDM; who has a genetic predisposition to Alzheimer's disease; who has a genetic factor that denotes increased risk of Alzheimer's disease, wherein the genetic factor may also comprise at least one ε4 allele or absence of an ε2 allele at the apolipoprotein E locus; who bears a biological marker that denotes increased risk of Alzheimer's disease; who has a behavioral state that denotes increased risk of Alzheimer's disease, and which may further comprise mild cognitive impairment (MCI); who is an age of 20 or older and prior to onset of clinical symptoms of Alzheimer's disease; who is an age of 40 or older and prior to onset of clinical symptoms of Alzheimer's disease; or who is over about 60 years old and free of clinical symptoms of Alzheimer's disease. The invention further provides a method of inhibiting a symptom of Alzheimer's disease in an individual by administering a therapeutically effective amount of a composition comprising D-pinitol, wherein the symptom is a cognitive impairment, which may further comprise a learning or memory deficit.

In another embodiment, the invention also provides a method of treating a symptom of Alzheimer's disease in an individual by administering a therapeutically effective amount of a composition comprising D-pinitol. In a further embodiment the method provides a composition that is pharmaceutically acceptable. In another aspect, the method comprises administering the composition prior to the onset of Alzheimer's disease. In yet another aspect, the method comprises administering the composition to an individual who is asymptomatic and at risk of developing Alzheimer's disease, with or without NIDDM; who has a genetic predisposition to Alzheimer's disease; who has a genetic factor that denotes increased risk of Alzheimer's disease, wherein the genetic factor may also comprise at least one ε4 allele or absence of an ε2 allele at the apolipoprotein E locus; who bears a biological marker that denotes increased risk of Alzheimer's disease; who has a behavioral state that denotes increased risk of Alzheimer's disease, and which may further comprise mild cognitive impairment (MCI); who is an age of 20 or older and prior to onset of clinical symptoms of Alzheimer's disease; who is an age of 40 or older and prior to onset of clinical symptoms of Alzheimer's disease; or who is over about 60 years old and free of clinical symptoms of Alzheimer's disease. The invention further provides a method of treating a symptom of Alzheimer's disease in an individual by administering a therapeutically effective amount of a composition comprising D-pinitol, wherein the symptom is a cognitive impairment, which may further comprise a learning or memory deficit.

In another embodiment, the invention provides a method of inhibiting amyloidosis in an individual by administering to the individual a therapeutically effective amount of a composition comprising D-pinitol. In a further aspect of this method, the individual has been diagnosed with Alzheimer's disease or is at risk of developing Alzheimer's disease. In another aspect of this method, the composition can be administered prior to the onset of Alzheimer's disease and may also be pharmaceutically acceptable. In yet another aspect, the method can be used to inhibit only that class of amyloidoses that are β-amyloidoses.

In still another embodiment, the invention provides a method of inhibiting the activity of γ-secretase in an individual by administering to the individual a therapeutically effective amount of a composition comprising D-pinitol. In a related aspect of the method, the individual can be diagnosed with Alzheimer's disease or be at risk of developing Alzheimer's disease. The method can further comprise administering the composition prior to the onset of Alzheimer's disease. In still another aspect, the invention provides a method of inhibiting the activity of γ-secretase in an individual by administering to the individual a therapeutically effective amount of a composition comprising D-pinitol that is also pharmaceutically acceptable.

In a different embodiment, the invention provides a method of treating a symptom of Alzheimer's disease in an individual by reducing the daily caloric intake of the individual. More specifically, the method can comprise reducing caloric intake of carbohydrates only, and if desired, by thirty percent.

In an alternative embodiment, the invention provides a method of preventing a symptom of Alzheimer's disease in an individual by reducing the daily caloric intake of the individual. In another aspect, the method may comprise reducing caloric intake of carbohydrates only, and if desired, by thirty percent.

In a different embodiment, the invention provides a method of treating a symptom of amyloidosis in an individual by reducing the daily caloric intake of the individual. In another aspect, the method may comprise reducing caloric intake of carbohydrates only, and if desired, by only thirty percent. In still another aspect, the amyloidosis is β-amyloidosis only.

In a different embodiment, the invention provides a method of inhibiting a symptom of amyloidosis in an individual by reducing the daily caloric intake of the individual. In another aspect, the method may comprise reducing caloric intake of carbohydrates only, and if desired, by only thirty percent. In still another aspect, the amyloidosis is β-amyloidosis only.

In yet another embodiment, the invention comprises a method of promoting healthy nervous system function in a mammal by administering a composition comprising D-pinitol to the mammal. In a further aspect, the mammal can be asymptomatic or not have a condition of insulin resistance, hyperlipidemia, or dyslipidemia. In yet another aspect, the mammal is a human. In still another aspect, the nervous system function can be a cognitive ability, which can further comprise learning or memory.

In yet another embodiment, the invention comprises a method of promoting healthy nervous system function in a mammal by administering a composition comprising D-pinitol to the mammal. In a further aspect, the mammal can be asymptomatic or not have a condition of insulin resistance, hyperlipidemia, or dyslipidemia. In still another aspect, the function of the nervous system may be function of the brain or even function of a sub-region of the brain, such as the hippocampus.

In another embodiment, the invention provide a method of studying the role of NIDDM in AD neuropathology by placing an animal on a diet sufficient to induce NIDDM-like insulin resistance, wherein the insulin resistance is associated with a symptom of Alzheimer's disease. In a further aspect, the animal may be a mammal, or more specifically a mouse, or even more specifically, the Tg2576 strain of mice.

In a related aspect of the invention, the symptom of Alzheimer's disease can be amyloidosis or an impairment of cognitive function generally or alternatively, just learning or memory.

In another embodiment, the invention provides a cell-free system for studying enzymatic cleavage of the amyloid precursor protein by α-, β-, or γ-secretase under conditions which allow the amyloid precursor protein to remain bound to its membrane under physiological conditions.

In still another embodiment, the invention provides a method of using the cell-free system to study amyloidosis by incubating the extract under physiological conditions and quantifying activity of a α-, β-, and γ-secretase.

In yet another embodiment, the invention provides a method of using the cell-free system to quantify activity of a α-, β-, and γ-secretase, by incubating the extract under physiological conditions.

In still another embodiment, the invention provides a method of using the cell-free system to screen for compound useful for preventing or treating an amyloidogenic disorder, by incubating the extract under physiological conditions in the presence of the compound; and quantifying activity of α-, β-, and γ-secretase.

The methods and pharmaceutical compositions of the invention include an effective amount of D-pinitol used in combination with a drug approved for treatment of Alzheimer's disease, such as donepezil (Aricept®), galantamine (Reminyl®), tacrine hydrochloride (Cognex®), and rivastigmine tartrate (Exelon®), and a pharmaceutically acceptable carrier.

The methods and pharmaceutical compositions of the invention include an effective amount of D-pinitol used alone or in combination with caloric restriction for prevention or treatment of mild cognitive impairment (MCI).

In preferred embodiments, the methods and pharmaceutical compositions of the invention provide a plasma or blood concentration of 10 micromolar D-pinitol, plus or minus 90%, 50%, 30%, 10%, 5% or 3%.

The above features and many other attendant advantages of the invention will become better understood by reference to the following detailed description when taken in conjunction with the accompanying drawings.

BRIEF DESCRIPTION OF THE DRAWINGS

FIG. 2 depicts data showing that diet-induced insulin resistance promotes amyloid burden in Tg2576 mice. (A) ELISA detection of $A\beta_{1-40}$ and $A\beta_{1-42}$ peptide content and 22C11-immunpositive holo-APP content in the hippocampal formation. (B) Stereological cerebral cortical (neocortex and hippocampal formation) 6E10-immunopositive amyloid plaque volume and burden (amyloid plaque volume as a percentage of cerebral cortex volume). In A-B, values represent means±s.e.m., n=5-6 per group; *P<0.05, P<0.01, *P<0.001 vs. control group (2-tailed Student's t test).

DETAILED DESCRIPTION OF THE INVENTION

Introduction

Figure 1:
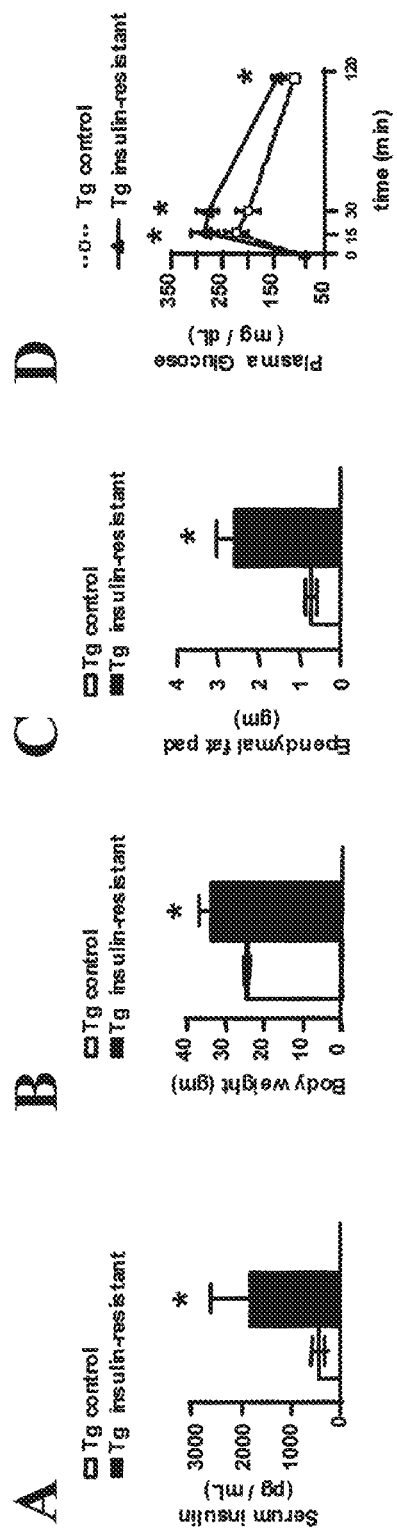
FIG. 1 depicts data showing that a high-fat diet induces insulin resistance in Tg2576 mice. Female Tg2576 (Hsiao et al. Science 1996; 274:99-102) mice were exposed to either the high-fat diet (Tg insulin-resistant group) or a standard rodent laboratory diet (Tg control group), starting at 3-4 months of age. Animals were then assessed for indexes of NIDDM-like insulin resistance at 9 months of age. (A) ELISA detection of serum insulin content. (B) Body weight. (C) ependymal fat-pad weight measurements. (D) Post-prandial intraperitoneal glucose tolerance response in which blood glucose content was monitored over time following an i.p. injection of glucose (2 g/kg BW). In A-D, values represent means±SEM (standard error of the mean) n=5-6 per group; *P<0.05 vs. control group (2-tailed Student's t test).

The present invention is based, in part, on the discovery that controlled dietary treatment of Tg2576 transgenic mice recapitulates the hallmarks of human non-insulin-dependent diabetes-mellitus (NIDDM) (e.g., insulin resistance, glucose intolerance, and increased body weight). The induction of NIDDM is accompanied by the premature appearance in the brain of pathological hallmarks associated with human Alzheimer's disease (AD), including aberrant accumulation of β-amyloid plaques, increased γ-secretase activity, and decreased insulin-degrading enzyme (IDE) activity. Moreover, the AD neuropathology is further accompanied by premature cognitive deficits, including specific disruptions of learning and memory.

In addition, the present invention is based on the discovery that molecules useful for controlling insulin resistance in NIDDM can inhibit or preclude appearance of biochemical, anatomical, and cognitive pathologies associated with AD. In particular, early treatment with D-pinitol reduces β-amyloidosis and restores signal transduction by both the insulin-receptor and glycogen synthase kinase-3.

Further, the present invention is based on the generation of a novel cell-free system, allowing for the first time, analysis of secretase-mediated cleavage of APP under physiological conditions that retain APP in its native membrane-bound conformation. In this system, D-pinitol inhibits β-amyloid with exquisite specificity, inhibiting the activity of γ-secretase but not that of α- and β-secretase.

Accordingly, the present invention provides a number of uses for D-pinitol. These include uses for the prevention, treatment, and management for diseases associated with β-amyloid accumulation. In addition to Alzheimer's, these disorders include, but are not limited to, MCI, Down's Syndrome, cerebral amyloid angiopathy, thrombolysis-related intracerebral haemorrhage, and other diseases involving beta-amyloid deposition. In particular, the present application provides methods for inhibiting the onset and progression of AD as well as methods of treating AD symptoms and AD disease. In another embodiment, the present invention provides methods based on the use of D-pinitol to inhibit amyloidosis and gamma-secretase activity in the nervous system, preferably the brain. More generally, the present invention provides methods for using D-pinitol compositions to treat MCI or to promote a healthy nervous system through its neuroprotective effects on neural structure and function.

The invention also provides animal systems for analyzing the mechanistic relationship between NIDDM and AD-type diseases. In addition, the present invention provides cell-free compositions that preserve the membrane-bound configuration of APP under physiological conditions. The invention provides uses of the cell-free system in analyzing the processing of APP and identifying modulatory compounds that target amyloidosis.

The present invention is also based, in part, on the finding that caloric restriction attenuates β-amyloid neuropathology in a mouse model of Alzheimer's disease. Accordingly, the invention provides methods to inhibit or treat AD and related disorders in an individual based on reducing caloric intake.

Definitions

As used herein, "D-pinitol" takes its ordinary meaning in the art.

As used herein, "mild cognitive impairment" or "MCI" takes its ordinary meaning in the art.

As used herein, an "individual" is preferably a mammal and more preferably a human, but can be any animal, including a laboratory animal in the context of a clinical trial or screening or activity experiment. Thus, as can be readily appreciated by one of ordinary skill in the art, the methods of the present invention are particularly suited to administration to any animal, particularly a mammal, and including, but not limited to domestic animals, wild animals and research animals.

As used herein, the term "inhibit" means preventing or delaying the onset or progression of one or more clinical symptoms of AD. Common early symptoms of Alzheimer's include confusion, disturbances in short-term memory, problems with attention and spatial orientation, personality changes, language difficulties, unexplained mood swings.

The term "therapeutically effective amount" is used herein to mean an amount or dose of d-pinitol that is effective to ameliorate, delay, or prevent any of the foregoing symptoms, behaviors or events associated with Alzheimer's disease or related neurodegenerative disorders. Alternatively, a therapeutically effective amount is sufficient to cause an improvement in a clinically significant condition in the individual.

As used herein, the phrase "pharmaceutically acceptable" refers to molecular entities and compositions that are "generally regarded as "safe," e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government of listed in the U.S. Pharmacopeia or other generally recognized pharmacopeia for use in animals, and more particularly in humans.

The term "treat" is used herein to mean to relieve or alleviate at least one symptom of a disease in a subject. Within the meaning of the present invention, the term "treat" also denotes to arrest, delay the onset (i.e., the period prior to clinical manifestation of a disease) and/or reduce the risk of developing or worsening a disease. For example, it is known that there is a familial pattern of AD, whereby first-degree biological relatives of children with AD is more common than in the general population.

The term promote as used herein means to have any positive effect or benefit. As used, the term is relative and does not necessarily mean to enhance or improve. For example, a composition that maintains a normal rate of neuronal loss with age could still be deemed as having a promoting effect.

The term "carrier" refers to a diluent, adjuvant, excipient, or vehicle with which the compound is administered. Such pharmaceutical carriers can be sterile liquids, such as water and oils, including those of petroleum, animal, vegetable, or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. For biological systems, the term "about" refers to an acceptable standard deviation of error, preferably not more than 2-fold of a give value. Numerical quantities given herein are approximate unless stated otherwise, meaning that the term "about" or "approximately" can be inferred when not expressly stated.

Molecular Biology

In accordance with the present invention there may be employed conventional molecular biology, microbiology, and recombinant DNA techniques within the skill of the art. The general genetic engineering tools and techniques discussed herein, including transformation and expression, the use of host cells, vectors, expression systems, etc., are well known in the art. (See, e.g., Sambrook et al. Molecular Cloning: A Laboratory Manual 3rd ed. (2001), Cold Spring Harbor Laboratory Press: Cold Spring Harbor, N.Y.; Ausubel et al. eds. Current Protocols in Molecular Biology (2005), John Wiley and Sons, Inc.: Hoboken, N.J.; Bonifacino et al. eds. Current Protocols in Cell Biology (2005), John Wiley and Sons, Inc.: Hoboken, N.J.; Coligan et al. eds. Current Protocols in Immunology (2005), John Wiley and Sons, Inc.: Hoboken, N.J.; Coico et al. eds. Current Protocols in Microbiology (2005), John Wiley and Sons, Inc.: Hoboken, N.J.; Coligan et al. eds. Current Protocols in Protein Science (2005), John Wiley and Sons, Inc.: Hoboken, N.J.; and Enna et al. eds. Current Protocols in Pharmacology (2005), John Wiley and Sons, Inc.: Hoboken, N.J.).

Therapeutic Methods

Disorders treatable by the compositions and methods of the invention include, but are not limited to, Alzheimer's disease, MCI, Down's Syndrome, cerebral amyloid angiopathy, and cerebral hemorrhage, as well as other diseases involving beta-amyloid deposition in other organs.

In particular, the present invention advantageously provides a method of inhibiting the onset of the symptoms of Alzheimer's disease or related disorders. In the case of AD, these symptoms may range in degree from mild or moderate to severe (clinically diagnosable Alzheimer's disease). The method comprises administering to an individual at risk of developing the disease a D-pinitol composition in an amount sufficient to prevent or delay onset of the symptoms.

The present invention also relates to methods for treating an individual who manifests one or more symptoms of Alzheimer's disease or a related neurodegenerative disorder, such as MCI. Such symptoms may be mild, moderate, or severe. The method comprises administering to an individual displaying such symptoms a therapeutically effective amount of D-pinitol, alone or in combination with another effective agent, which is sufficient to alleviate or slow the progression of one or more symptoms, or to alleviate or slow the progression of the disease.

The concentration of D-pinitol depends on the desired dosage and administration regimen. In one preferred embodiment, the concentration of D-pinitol in blood or plasma is 10 micromolar±50%.

The route of administration may be oral, parenteral, transmucosal, intranasal, rectal, vaginal, or transdermal. Oral is preferred. Parental routes include intravenous, intra-arteriole, intramuscular, intradermal, subcutaneous, intraperitoneal, intraventricular, intrathecal, and intracranial administration.

The pharmaceutical composition may also include other biologically active substances in combination with the compound.

The pharmaceutical composition can be added to a retained physiological fluid such as blood or synovial fluid. For CNS administration, a variety of techniques are available for promoting transfer of the therapeutic agent across the blood brain barrier, including disruption by surgery or injection, co-administration of a drug that transiently opens adhesion contacts between CNS vasculature endothelial cells, and co-administration of a substance that facilitates translocation through such cells.

In another embodiment, the therapeutic agent can be delivered in a controlled release manner. For example, a therapeutic agent can be administered using intravenous infusion with a continuous pump, in a polymer matrix such as poly-lactic/glutamic acid (PLGA), in a pellet containing a mixture of cholesterol and the active ingredient (SilasticR™; Dow Corning, Midland, Mich.; see U.S. Pat. No. 5,554,601), by subcutaneous implantation, or by transdermal patch.

Preferably, the optimal therapeutically effective amount should be determined experimentally, taking into consideration the exact mode of administration, the indication toward which the administration is directed, the subject involved (e.g., body weight, health, age, sex, etc.), and the preference and experience of the physician or veterinarian in charge.

The effective agent may be combined with a pharmaceutically acceptable carrier, which term includes any and all solvents, dispersion media, coatings, anti-oxidants, isotonic and absorption delaying agents and the like. The use of such media and agents for pharmaceutically active substances is well known in the art. Except insofar as any conventional media or agent is incompatible with the active ingredient, its use in the therapeutic compositions and methods described herein is contemplated. Supplementary active ingredients can also be incorporated into the compositions.

The formulation may be prepared for use in various methods for administration. The formulation may be given orally, by inhalation, applied topically or may be injected, e.g. intravascular, intratumor, subcutaneous, intraperitoneal, intramuscular, etc.

The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semiweekly, etc. to maintain an effective dosage level. In some cases, oral administration will require a higher dose than if administered intravenously.

The effective agent of the invention can be incorporated into a variety of formulations for therapeutic administration. More particularly, the complexes can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

D-pinitol

Pinitol and derivatives and metabolites thereof were known to be useful prior to the invention in certain nutritional and medicinal compositions, such as for diabetes mellitus and its chronic complications, but not AD or MCI. Pinitol and its derivatives or metabolites are available from a number of natural sources (such as, for example, pine needles, chick peas, Bougainvillea leaves, alfalfa, soy beans and other legumes) and synthetic processes. Use of D-pinitol for the treatment of disorders associated with resistance to insulin is described, for example, in WO 96/29063.

Methods of Promoting a Healthy Nervous System

The present invention relates further to a general method of promoting a healthy nervous system by administration of active ingredient compositions comprising D-pinitol. Such methods promote normal structure and function of the nervous system, which is critical for cognitive processes, such as learning and memory, as well as emotional well-being.

The compositions of the present invention are intended for administration to a mammal, in particular a human being, in a suitable dosage form as is known in the art. Suitable dosage forms known in the art include parenteral, enteral, and especially oral. Oral solid and liquid dosage forms are particularly preferred.

Oral solid dosage forms are well known in the art and include tablets, caplets, gel caps, capsules, and edible food items. Oral solid dosage forms can be made with one or more pharmaceutically acceptable excipients. Pharmaceutically acceptable excipients assist or make possible the formation of a dosage form for a bioactive material and include diluents, binding agents, lubricants, glidants, disintegrants, coloring agents, and flavorants and nutrients. An excipient is pharmaceutically acceptable if, in addition to performing its desired function, it is non-toxic, well tolerated upon ingestion, and does not interfere with absorption of bioactive materials.

Tablets can be made by well-known compression techniques using wet, dry, or fluidized bed granulation methods. For example, the ingredients are mixed in a blender. Useful blenders include the twin-shell type, the planetary mixer type, and the high-speed high-shear type; all of which are known to the skilled artisan. The blended combination is sieved and dried to a granulate. The granulate is then compressed into tablets using a tableting press as is known in the art. Preferably, the granulate is sieved before the compression to make sure that the granulate has the desired particle size.

D-Pinitol, a Natural Insulin Sensitizer Agent: Implications for AD Treatment

The insulin sensitizer agent D-pinitol, which is structurally related to the phosphatidylinositol phosphates that participate in insulin-mediated stimulation of glucose transport (Holman and Kasuga. Diabetologia 1997; 40:991-1003; White. Diabetologia 1997; 40(Suppl2):S2-17), may beneficially influence AD-type amyloid neuropathology through inhibition of γ-secretase activity in the brain resulting in reduced generation of amyloidogenic $A\beta_{1-42}$ and $A\beta_{1-40}$ peptides. D-pinitol is found in high concentrations in pine tree components (Asiegbu. FEMS Microbiol. Ecol 2000; 33:101-110) and is present at about 1% dry weight in soy (Davis et al. Diabetes Care 2000; 23:1000-1005). In Indonesia, about 2 million metric tons of soy were consumed in 1994 by a total population of 200 million (Davis et al. Diabetes Care 2000; 23:1000-1005). This converts to an average intake of 25-30 grams of soy per day per person or about 250-300 mg of pinitol, which is about 4 mg/kg/day in a 70 kg individual. This daily dose range of pinitol is therefore considered safe as evidenced by centuries of soy intake. In a like manner, a serving containing over 100 grams (about ¼ pound) of soy per day, which is a reasonable portion for some individuals, would provide about 1 gram of pinitol or a dose level of over 10 mg/kg in a 70 kg individual. While crude soy preparations are not substantially pure and may not provide the most readily or rapidly assimilated form of pinitol, it is obvious that pinitol consumption through soy is substantial. Thus, by history of use, animal and human clinical scientific studies, D-pinitol is non-toxic and safe in man.

D-Pinitol has a demonstrated blood glucose lowering and insulin function enhancing effect. Thus, dietary supplementation of pinitol may be recommended to help maintain normal metabolic function (Davis et al. Diabetes Care 2000; 23:1000-1005; Larner. IUBMB Life 2001; 51:139-148; Bates et al. Br. J. Pharmacol. 2000; 130:1944-1948). D-pinitol also has been identified in putative insulin mediator fractions that have hypoglycemic activity, and appears to act downstream in the insulin-signaling pathway to mimic the effects of insulin (Larner. IUBMB Life 2001; 51:139-148; Bates et al. Br. J. Pharmacol. 2000; 130:1944-1948). Administration of D-pinitol has been shown to lower blood glucose concentration in streptozotocin-induced diabetic rats and in normal rats given glucose (Bates et al. Br. J. Pharmacol. 2000; 130:1944-1948; Lamer et al. J. Med. Chem. 2003; 46:3283-3291; Ortmeyer et al. Endocrinology 1993; 132:646-65). This isomer also increased the rate of glucose disappearance in insulin-resistant and hyperinsulinemic monkeys (Ortmeyer et al. Endocrinology 1993; 132:646-651; Ortmeyer et al. Endocrinology 1993; 132:640-645), suggesting that the D-pinitol itself might improve glucose metabolism. Consistent with this evidence, supporting the feasibility of the proposed studies, we found in preliminary studies that treatment with safe doses of D-pinitol in the drinking water (80 mg/kg body weight, per day) promotes cognitive functions in Tg2576 mice that model AD neuropathology and memory impairment.

Cell-Free Systems, Screening Methods, Assays, and Animal Systems

The present invention further provides cell-free systems and methods for identifying a candidate compound useful for modulating the production of β-amyloid. These systems are described in detail in the Examples which follow.

The methods of the present invention can be used to identify a candidate compound useful to treat a condition that can be treated by modulating the levels of beta-amyloid.

The test compound can be, without limitation, a small organic or inorganic molecule, a polypeptide (including an antibody, antibody fragment, or other immunospecific molecule), an oligonucleotide molecule, a nucleic acid molecule, or a chimera or derivative thereof.

Furthermore, the present invention relates to the use of an animal model of studying the impact of NIDDM on Alzheimer's disease. In addition, the present invention provides a cell-free system that faithfully carries out γ-secretase-mediated cleavage of the APP protein under physiological conditions.

EXAMPLES

The following Example(s) are understood to be exemplary only, and do not limit the scope of the invention or the appended claims.

Example 1

Confirmation of Diet-Induced NIDDM-Like Insulin Resistance in Tg2576 Mice

Background

Type II diabetes (a non-insulin dependent form of diabetes mellitus (NIDDM) is characterized by glucose intolerance, obesity, and hyperinsulinemia. Studies of the proposed mechanistic link between NIDDM and AD first required confirmation of diet-induced NIDDM-like insulin resistance in the AD susceptible transgenic mouse strain Tg2576.

Materials and Methods

Female Tg2576 mice (Hsiao et al. Science 1996; 274:99-102) were exposed to either a high-fat diet (Tg insulin-resistant group) or a standard rodent laboratory diet (Tg control group), starting at 3-4 months of age. At 9 months of age, animals were then assessed for indexes of NIDDM-like insulin resistance, including insulin content, body weight, fat measurements, and glucose tolerance.

Results and Discussion

FIG. 1 shows that administration of a high fat diet, as described in the Materials and Methods, gives rise to the hallmarks of NIDDM: increased levels of serum insulin (FIG. 1A); increased body weight (FIG. 1B); increased weight of the ependymal fat-pad (FIG. 1C); and increased levels of plasma glucose (FIG. 1D).

Example 2

Diet-Induced NIDDM-Like Insulin Resistance Promotes AD-Type Amyloid Burden in Tg2576 Mice Background As shown in FIG. 1, dietary conditions in insulin-resistant Tg2576 mice recapitulated the cardinal features of human-NIDDM, including hyperinsulinemia, increased body weight, and glucose intolerance, relative to the normoglycemic control mouse group. The present study addressed the hypothesis that these altered metabolic conditions might also causally promote AD-type amyloidosis in Tg2576 mice.

Materials and Methods

Nine-month old insulin-resistant and normoglycemic Tg2576 female mice were assessed for indexes of AD-type amyloid burden in the brain, as shown in FIG. 2.

Results and Discussion

Five months of exposure to a high-fat diet resulting in NIDDM-like insulin resistance conditions promoted a greater than two-fold elevation in amyloidogenic $A\beta_{1-40}$ and $A\beta_{1-42}$ peptide content in the hippocampal formation of 9-month old Tg 2576 mice, relative to normoglycemic Tg2576 control mice ($P<0.05$) (FIG. 2A). No detectable alteration in 22C11-immunoreactive total holo-APP steady-state level was found in the hippocampal formation of insulin-resistant relative to normoglycemic Tg2576 mice (FIG. 2A). Moreover, consistent with the evidence that diet-induced NIDDM-like insulin resistance promoted amyloidogenic $A\beta$ peptide accumulation in the hippocampal formation, we found a ~2 fold increase in cerebral cortical AD-type amyloid (6E10-immunopositive) plaque burden (plaque volume as percentage of the total cerebral cortical volume; $P<0.05$) (FIG. 2B), relative to normoglycemic Tg2576 mice. The increased volumetric cerebral cortical amyloid plaque burden in the insulin-resistant Tg2576 mice was characterized by larger AD-type (6E10 immunoreactive) amyloid plaque volume ($P<0.001$) rather than increased number of AD-type amyloid plaques (FIG. 2B). Thus, it is possible that diet-induced insulin resistance exacerbates amyloidosis through mechanisms involved in $A\beta$ peptide generation.

Subsequent experiments addressed the molecular mechanisms through which NIDDM-like insulin resistance promoted AD-type amyloidosis. The results revealed that dietary conditions leading to NIDDM-like insulin resistance in Tg2576 mice is associated with decreased IR signaling in the brain (data not shown; Ho et al. FASEB J. 2004; 18: 902-904). Moreover, the NIDDM-like insulin resistance in the brain resulted in altered regulation of AKT/PKB and GSK-3α and GSK-3β phosphorylation (data not shown). This evidence suggests that diet induced NIDDM-like insulin in Tg2576 mice is associated with decreased AKT/PKB activity leading to GSK-3 activation. More specifically, insulin resistance conditions may specifically promote GSK-3α and GSK-3β activities through attenuation of AKT/PKB mediated $pS^{21}$-GSK-3α and $pS^9$-GSK-3β phosphorylation in the brain.

Example 3

NIDDM-Like Insulin Resistance Promotes γ-Secretase Activity, which Correlates with $pS^{21}$-GSK-3α and $pS^9$-GSK-3β Phosphorylation Background Based on the evidence that NIDDM-like insulin resistance results in activation of GSK-3α and GSK-3β activities in the brain of Tg2576 mice disclosed above and on recent studies suggesting that activation of GSK-3 (GSK-3α) can promote $A\beta$ peptide generation (Phiel et al. Nature 2003; 423:435-439), subsequent experiments addressed the role of NIDDM-like insulin resistance on γ-secretase activity in the brain and its relationship with GSK-3α and GSK-3β activities.

Materials and Methods

The activity of γ-secretase was measured by an established enzymatic assay (Shearman et al. Biochemistry 2000; 39:8698-8704), which is based on detection of the ~7 kDa carboxy terminal fragment (CTF)-γ formation from membrane-bound APP.

Results and Discussion

Figure 3:
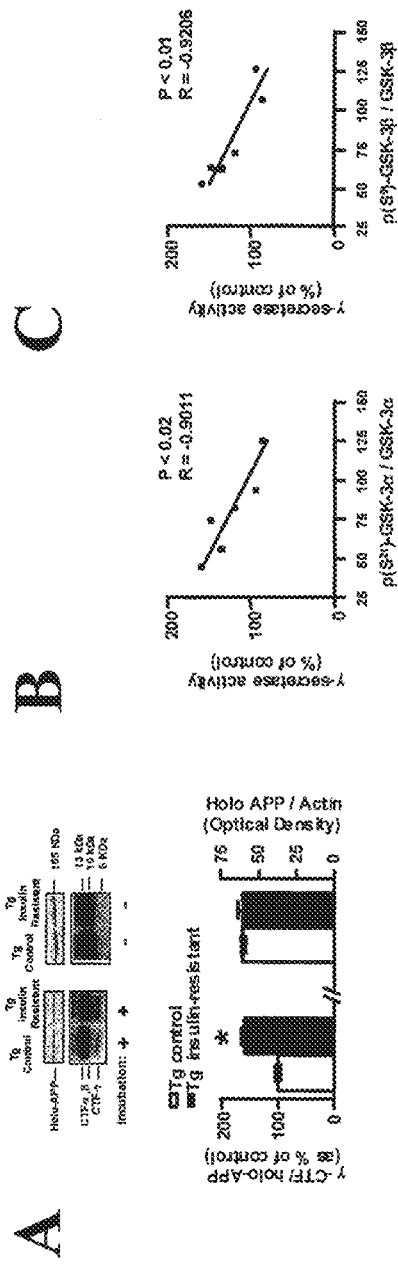
FIG. 3 depicts data showing that insulin resistance promotes γ-secretase activity in the brain of Tg2576 mice. (A) Increased γ-secretase activity in cerebral cortex (left panel) assessed by generation of γ-CTF from membrane associated APP (normalized to holo-APP in the membrane preparation). Parallel western blot analysis of holo-APP from total brain extract (right panel) confirmed that the diet-induced insulin resistance did not influence holo-APP expression; (A inset), representative cleavage products generated from membrane-bound APP; as expected, negative controls (no incubation) yielded no CTF-γ cleavage product. (B-C) Scatter plot analysis of γ-secretase activity as a function of $pS^{21}$-GSK-3α/GSK-3β (B) and $pS^9$-GSK-3α/GSK-3β (C). Straight line represents best linear regression fit.

Insulin-resistant Tg2576 mice exhibited ~2 fold increased generation of cerebral cortical CTF-γ ($P<0.05$), in the absence of changes in steady-state holo-APP (22C11 immunopositive) content compared to normoglycemic Tg2576 mice (FIG. 3A). Most interestingly, the level of $pS^{21}$-GSK-3α and $pS^9$-GSK-3β phosphorylation (relative to total GSK-3α and GSK-3β) in the cerebral cortex positively correlated with the generation of brain C-terminal fragment (CTF)-γ cleavage product of APP, an index of γ-secretase activity, in the brain of insulin-resistant Tg2576 mice ($pS^{21}$-GSK-3α: Pearson $r=-0.9011$, $P<0.02$; $pS^9$-GSK-3β: Pearson $r=-0.9206$, $P<0.01$) (FIGS. 3B-C).

This evidence supports the hypothesis that the activation of GSK-3α and GSK-3β (reflected by decreased $pS^{21}$-GSK-3α and $pS^9$-GSK-3β phosphorylation) may be a mechanism through which insulin resistance may promote the generation of $A\beta$ peptides in the brain. This evidence suggests that in Tg2576 mice, dietary conditions leading to NIDDM-like insulin resistance may result in altered IR signaling in the brain and eventually "unleash" GSK-3α and GSK-3β activity capable of promoting γ-secretase activity and the generation of amyloidogenic $A\beta$ peptides. Further support derives from the analysis of 12-month old insulin resistant- and control normoglycemic-Tg2576 mice for indices of IR signaling and GSK-3 activity in the cerebral cortex. Compared with controls, the insulin-resistant mice showed a ~2-fold reduction of $Y^{1162/1163}$-IRβ autophosphorylation (an index of reduced IRβ activation) coinciding with a decrease in PI3K-(p85) and $pS^{473}$-AKT (data not shown). This is indicative of reduced PI3K-AKT signaling in the brain of insulin-resistant versus normogylcemic Tg2576 mice. Compared to normoglycemic controls, the brain of insulin-resistant Tg2576 mice also showed decreased $pS^{21}$-GSK-3α and $pS^9$-GSK-3β phosphorylation (indicative of GSK-3 activation) coinciding with increased γ-secretase activity (data not shown).

Example 4

Diet-Induced NIDDM-Like Insulin Resistance Accelerates Cognitive Impairment in Insulin-Resistant Tg2576 Mice Relative to Normoglycemic Tg2576 Mice Background Based on the previous results showing that diet-induced NIDDM-like insulin resistance coincided with promotion of cortical AD-type amyloidosis, and the existing evidence that AD type amyloidosis correlates with cognitive impairment in Tg2576 mice (Kawarabayashi et al. J. Neurosci. 2001; 21:372-381; King and Arendash. Physiol Behay. 2002; 15:627-642), the present studies addressed the possibility that the increased AD-type amyloidosis might have accelerated cognitive impairment in 9-month Tg2576 mice, which are otherwise not behaviorally impaired at this age (King and Arendash. Physiol Behay. 2002; 15:627-642).

Materials and Methods

In this study, nine-month old Tg2576 female mice (n=5-6 per group) were trained for eight days in a hidden platform version of the water maze. Twenty-four hours following the learning phase, a probe trial was conducted wherein the platform was removed.

Results and Discussion

Figure 4:
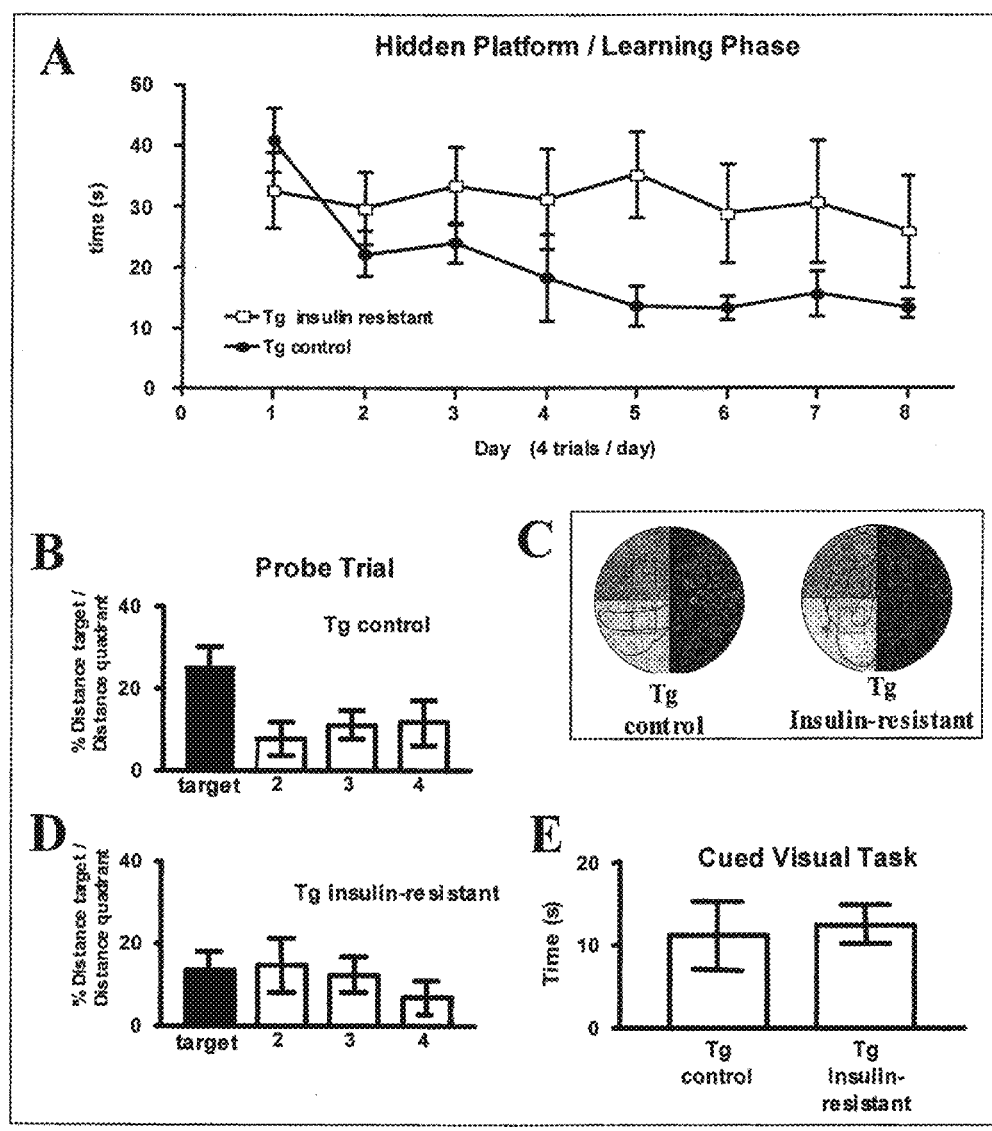
FIG. 4 depicts data showing that insulin-resistant Tg2576 mice exhibit impaired ability to learn in a Morris spatial water maze task. (A) Tg2576 control mice improved their latencies during the learning phase of testing (repeated measures ANOVA P<0.001, $F_{7,28}=5.04$), while insulin-resistant Tg2576 mice were impaired in their ability to learn the task and displayed consistently longer latencies throughout testing relative to control Tg2576 mice (two-way ANOVA P<0.0017, $F_{1,72}=10.76$ for diet treatment). (B) Tg2576 control mice displayed a significant bias for the former platform location shown in (C), suggesting that their superior performance in the learning phase coincided with acquisition and retention of the spatial location of the escape platform. (D) Insulin-resistant Tg2576 mice swam in a random manner depicted in (C), during the probe trial, further suggesting that diet-induced insulin resistance led to an impaired ability to learn this task. (E) During probe trial, both groups exhibited equivalent latencies, suggesting that deficits observed in insulin-resistant Tg2576 mice were unlikely to have arisen from impaired swimming or visual ability.

Nine-month old insulin-resistant Tg2576 mice exhibited impaired ability to learn in a Morris spatial maze task relative to control age-gender matched normoglycemic Tg2576 mice. In particular, we found that insulin-resistant Tg2576 mice exhibited longer escape latencies during a hidden platform-learning phase of testing (which is an index of hippocampal memory dysfunction severely affected in AD) compared to control Tg2576 mice fed standard rodent laboratory diet (FIG. 4A). Moreover, this apparent impairment in learning coincided with a lack of navigation bias (FIGS. 4B-D) for the former platform location in a probe trial, wherein the escape platform was removed 24 h following the learning phase.

This evidence suggests that diet-induced NIDDM-like insulin resistance induced a deficit in spatial learning in Tg2576 mice in the absence of changes to baseline visual ability (assessed in a cued version of the swim task; FIG. 4E) or motor activity (not shown). The study provided the basis to further explore the role of D-pinitol in this setting.

Example 5

Treatment of Tg2576 Mice with D-Pinitol Reduces Insulin-Resistance-Mediated Promotion of β-Amyloidosis in the Brain

Background

Given that insulin resistance promotes β-amyloid accumulation in Tg2576 mice that model AD type neuropathology (FIG. 2; Ho et al. FASEB J. 2004; 18:902-904), the present experiments tested whether treatment of Tg2576 mice with insulin sensitizing agent D-pinitol might ameliorate the β-amyloid pathology in different regions of the brain.

Materials and Methods

This study assessed Aβ peptide contents in the brain and in the periphery (serum) of 12-month old female Tg2576 mice in response to chronic treatment, initiating at 4 month of age, with a high-fat (HF) diet or HF diet plus pinitol (N=3-4 per group). Gender-age-matched Tg2576 mice maintained on standard rodent laboratory diet (LF diet) served as controls. High-fat diet and standard laboratory diet containing equal % of cholesterol per g/diet were purchased from Research Diet, Inc. (New Brunswick, N.J.) (Ho et al, FASEB J 2004; 18:902-204). Pinitol (Humanetics Corp.) was provided by incorporation into drinking water (600 mg pinitol/liter water), which is available ad libitum. Based on the assumption that an adult mouse drinks 5-ml of water per day, and that the body weight of an adult mouse is 30 gm, we estimated each mouse received 100 mg pinitol per kg body weight per day. Twelve-month old mice were sacrificed by decapitation. Blood was collected, clotted in room temperature for 15 min and centrifuged at 3,000×g for 20 min to separate the serum. Serum specimens were collected and stored at −80° C.

For quantitative assessment of Aβ peptides (Xiang et al. Gene Expr. 2002, 10:271-278), frozen pulverized brain tissues were homogenized in 5.0 M guanidine buffer, diluted (1:10) in phosphate-buffered saline containing 0.05% (v/v) Tween-20 and 1 mM Pefabloc protease inhibitors (Roche Biochemicals, Indianapolis, Ind.) and centrifuged for 20 min at 4° C. Total $A\beta_{1-40}$ or $A\beta_{1-42}$ was measured by sandwich ELISA (BioSource, Camarillo, Calif.) according to the manufacturer's instructions. Serum specimens were assessed directly using the same ELISA according to the manufacturer's instructions.

Results and Discussion

Figure 5:
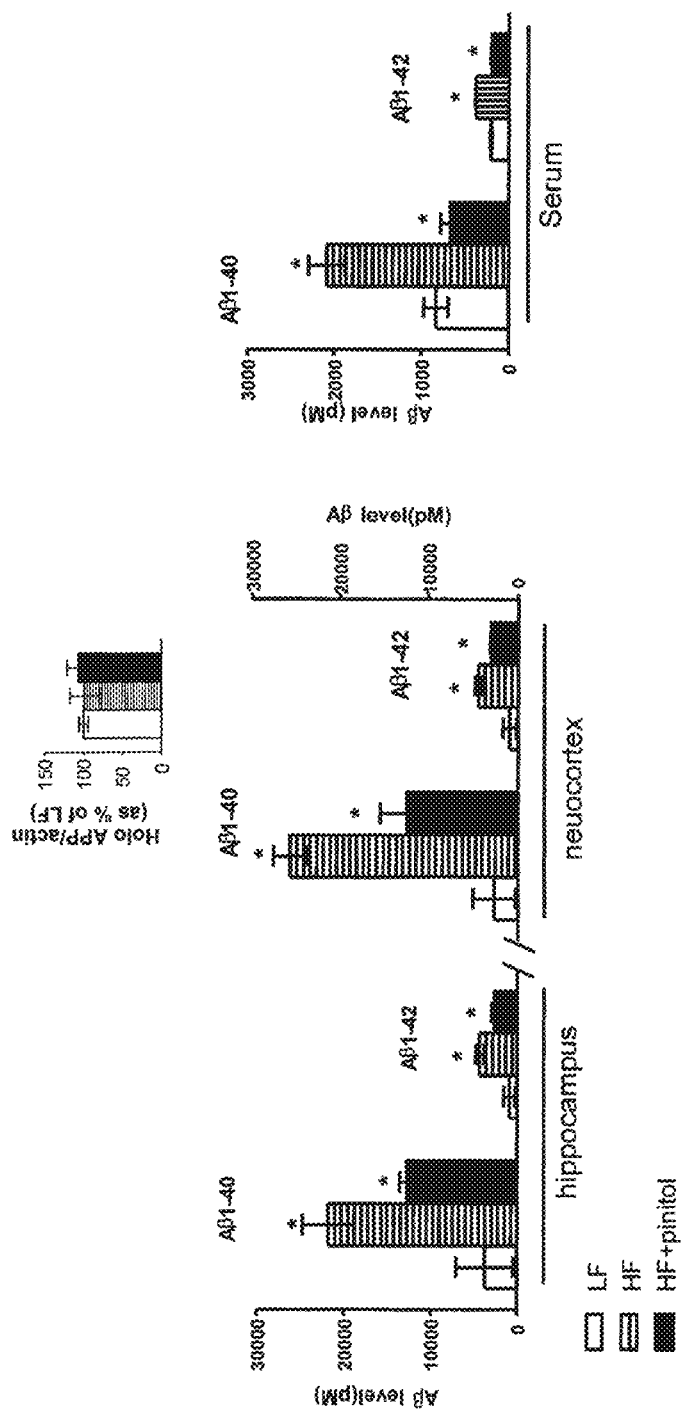
FIG. 5 depicts data showing that pinitol treatment reduced insulin-resistance mediated promotion of β-amyloidosis in Tg2576 AD mice.

The results show amelioration of β-amyloidogenesis in all regions of the brain tested (FIG. 5). Moreover, the anti-amyloidogenic activity of D-pinitol in Tg2576 mice is also associated with the restoration in the brain of (i) insulin receptor signal transduction; and (ii) GSK-3 activity. Indeed, D-pinitol treatment at 80 mg/kg/day D-pinitol in the drinking water beginning at six months of age increased $y^{1162/1163}$-phosphorylated IRβ (but not total IRβ) as well as PI3K-p85α and $S^{473}$-AKT in 12-month old Tg2576 mice, compared to insulin resistant and control Tg2576 mice.

Example 7

D-Pinitol Selectively Inhibits γ-Secretase Activity in Cultured Cells

Background

Figure 6A:
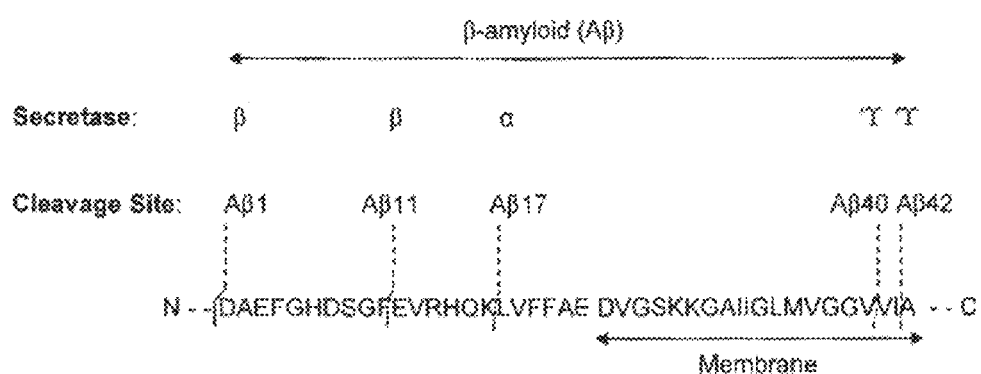
FIG. 6 depicts two representations of the β-amyloid precursor protein (βAPP) protein, emphasizing different features pertinent to the invention. (A) C-terminal region of βAPP, showing the membrane spanning region, sites of cleavage by α-, β-, and γ-secretases, and the sequence of β-amyloid (SEQ ID NO: 1). (B) Diagrammatic representation of in vitro γ-secretase assay based on generation of the P7 (γ-CTF) fragment from the amyloid precursor protein (APP) (Sastre et al. EMBO Rep. 2001; 2:835-841).
Figure 6B:
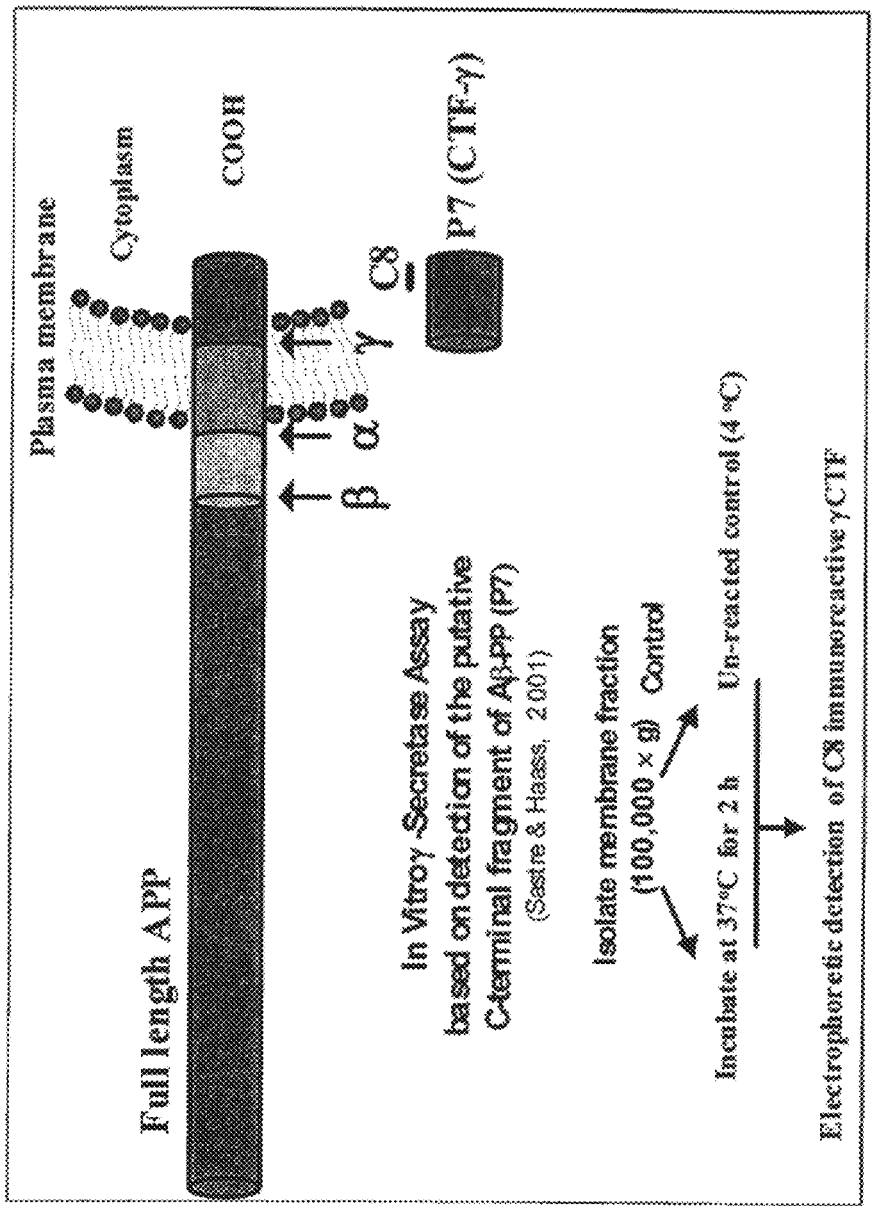

The observation that D-pinitol beneficially influences cognitive impairment in NIDDM-like insulin resistant TG2576 mice prompted exploration of the potential role of D-pinitol in mechanisms associated with generation of amyloidogenic Aβ peptides in an in vitro model of amyloidosis. The generation of Aβ from APP requires at least two proteolytic enzymes referred to as β- and γ-secretase. β-secretase mediates the N-terminal cleavage of APP producing C-terminal fragment (CTF)-β, which is the immediate precursor for intra-membranous cleavage by γ-secretase. The γ-secretase cut liberates AD from the membrane and generates an intracellular APP CTF-γ fragment, which represents the carboxyl terminal counterpart of Aβ (see FIG. 6). A third proteolytic enzyme, α-secretase, may be responsible for breaking down Aβ peptides.

The activity of γ-secretase is of great importance for two reasons: firstly, this enzyme (in conjunction with β-secretase) is essential to Aβ generation; and secondly γ-secretase cleavage determines the amyloidogenicity of the Aβ peptide to be formed (i.e. Aβ1-38, Aβ1-40, Aβ1-42). For these reasons, γ-secretase inhibition is currently thought to be a major therapeutic target for Aβ lowering strategies.

Materials and Methods

Cell-Based Secretase Assays

Figure 7:
FIG. 7 depicts data showing that D-pinitol does not influence α- and β-secretase activity, but has a robust inhibitory effect on γ-secretase activity in H4-APPswe cells. (A) α-secretase. (B) β-secretase. (C) γ-secretase ($A_{1-40}$). (D) γ-secretase ($A_{1-42}$).

In this study, cultured human glioma H4-cells with constitutive $APP_{751}$ expression were treated with increasing concentrations of pinitol, and then cellular α- and β-secretase activity as well as Aβ peptide contents in the conditioned media were assessed in response to pinitol treatment over time. Growth and maintenance of H4-$APP_{751}$ cells were as described in Qin et al. (J. Biol. Chem. 2002; 278:50970-50977). Confluent cell cultures were treated with increasing concentration of pinitol. At 24 and 48 hours after pinitol treatment, cells were harvested for secretase activity assays and conditioned media were collected for measurement of Aβ peptide contents. The α-secretase (FIG. 7A) and β-secretase (FIG. 7B) activities in pinitol-treated cells were measured using commercially available kits (R&D Systems). Harvested cells were homogenized in supplied buffers and homogenate was added to a secretase-specific APP peptide conjugated to the reporter molecules EDANS and DABCYL. In the uncleaved form, the fluorescent emissions from EDANS are quenched by the physical proximity of the DABCYL moiety, which exhibits maximal absorption at the same wavelength (495 nm). Cleavage of the peptide by the secretase physically separates the EDANS and DABCYL, allowing the release of a fluorescent signal. The level of α-secretase (FIG. 7A) or β-secretase (FIG. 7B) enzymatic activity is proportional to the fluorometric reaction in the homogenate. These data depict the content of $A\beta_{1-40}$ (FIG. 7C) and $A\beta_{1-42}$ (FIG. 7D) peptides in the conditioned culture media in response to pinitol treatment over time. Aβ peptides were measured by ELISA as described above. In FIG. 7, each value represents Mean±SEM; n=4 cultures per assay; *P<0.05 vs. control (no pinitol treatment) group (2-tailed Student's t test).

In-Vitro Model of Amyloidosis

For assessment of γ-secretase activity, cell monolayers were rinsed twice with ice-cold PBS on ice, scraped from tissue culture dishes and centrifuged (1,500 rpm, 10 min, 4° C.). Cell pellets were then resuspended (0.5 ml/10 cm dish) in homogenization buffer (10 mM MOPS pH 7.0, 10 mM potassium chloride, 1× complete protease inhibitor (PI) (Roche Molecular Biochemicals, Germany) and homogenized by passing cell suspensions through a 23-gauge needle 10 times. Homogenates were then centrifuged (2,500 rpm, 15 min at 4° C.) to remove unbroken cells and nuclei. The supernatant (membrane and post-nuclear supernatant) was then centrifuged (14,000 rpm, 20 min, 4° C.) and rinsed in homogenization buffer. Membranes were then resuspended (0.5 ml/10 cm dish) in assay buffer (150 mM sodium citrate pH 6.4; 1×PI) and incubated at (2 hr) at 37° C. in 25 μl of incubation buffer per assay sample to allow for generation of the CTF-γ cleavage product; negative control samples were maintained on ice. CTF-γ cleavage products (as well as CTF-α and CTF-β) were resolved electrophoretically in 10-20% Tris-Tricine gels (Bio Rad Laboratories, CA), and identified using an anti APP polyclonal C8 antibody. Immunoreactivities were visualized autoradiographically using a chemiluminescence detection kit (SuperSignal; Pierce Biotechnology, Rockford, Ill.). Aβ1-40 was also assayed by ELISA in the tissue culture preparations used for γ-secretase activity. Bar graphs represent Mean±SEM; n=4*P<0.01 vs. vehicle treated cells (PBS).

Results and Discussion

Figure 8:
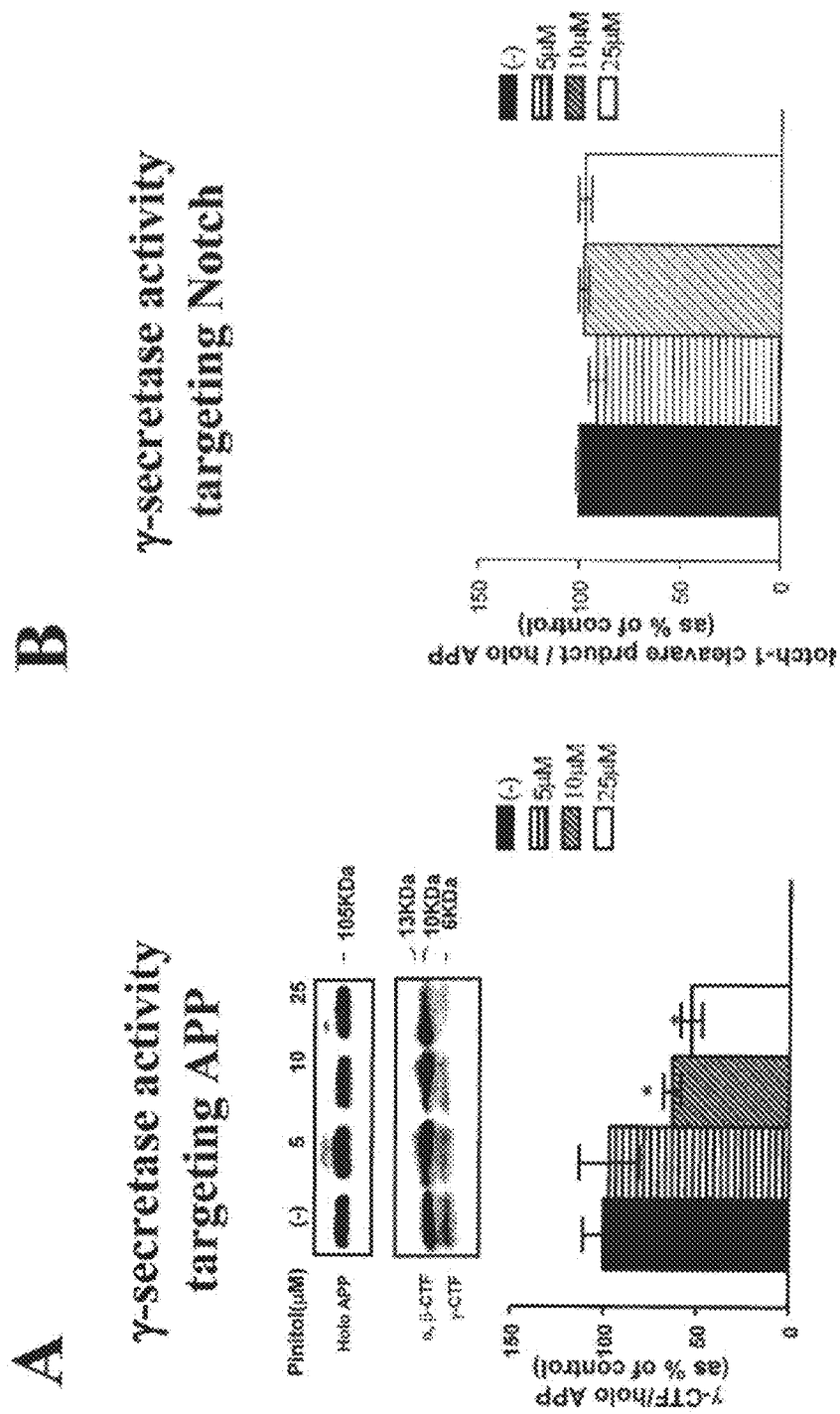
FIG. 8 depicts data showing that anti-amyloidogenic activity of D-pinitol is associated with selective reduction of γ-secretase-mediated APP cleavage in H4-APPswe cells. (A) APP (B) NOTCH

Dose-dependent studies of D-pinitol administration in cultured cells showed no effect on α- or β-secretase activity (FIGS. 8A-B). In contrast, these studies did reveal a robust effect on γ-secretase activity, leading to a dose-dependent inhibition of both $A\beta_{1-40}$ and $A\beta_{1-42}$ production (FIGS. 8C-D).

The selective effect of D-pinitol on γ-secretase activity was further analyzed with a powerful in vitro amyloidosis system developed by the inventors. Unlike conventional cell-free assays, this in vitro γ-secretase assay detects enzymatic cleavage under physiologic conditions, wherein APP and/or CTF-β are cleaved while membrane bound. The ~7 kDa CTF-γ APP fragment is readily segregated away from other CTFs generated by α- and β-secretase (CTF-α and CTF-β, respectively) (see FIG. 6). Quantification of CTF-γ provides a direct assessment of γ-secretase activity. As shown in FIG. 8A, the formation of the ~7 kDa CTF-γ APP fragment in H4-APPswe cells was blocked by treatment with D-pinitol in a dose-dependent manner, supporting the specificity of D-pinitol on γ-secretase activity. In contrast, d-chiro-inositol (DCI), a metabolite of D-pinitol, showed no inhibitory effect on β-amyloid formation in the in vitro system.

As independent corroboration of these findings, formation of the ~7 kDa CTF-γ APP was also blocked in a dose dependent fashion in extracts obtained from CHO-APPswe cells, and this reduction coincided with a corresponding reduction of Aβ1-40 peptide in the same tissue culture (data not shown). Furthermore, control studies, based on the LDL assay, revealed no detectable cell toxicity following D-pinitol treatment at all concentration tested (at 50-250 μM) as assessed by the LDH assay (not shown).

The selectivity of D-pinitol action was further addressed by examining its effect on cleavage of the signaling molecule NOTCH. The "gamma-secretase" complex, consisting of presenilins (PS), nicastrin (NCT), APH-1 and PEN-2, catalyzes the intramembranous proteolysis of truncated Notch derivatives to generate NICD, respectively. In contrast to its effect on APP, D-pinitol had no inhibitory effect on cleavage of NOTCH (FIG. 8B). In accord with these observations, D-pinitol also had no inhibitory effect on cleavage of NOTCH in the neocortex of Tg2576 transgenic mice, compared to insulin-resistant and control Tg2576 mice (data not shown).

Example 8

Caloric Restriction Attenuates β-Amyloid Neuropathology in a Mouse Model of Alzheimer's Disease Background Recent prospective studies indicate that increased caloric intake is a risk factor for Alzheimer's disease (AD). While there is evidence supporting a potential neuroprotective role of caloric restriction (CR) in the brain (Cummings. N. Engl. J. Med. 2004; 315:56-67; Anson et al. Proc. Natl. Acad. Sci. USA 100; 6216-6220), there is no information whether a CR regimen may influence AD. A fundamental problem in AD is the aberrant generation of amyloidogenic β-amyloid peptides in the brain leading to abnormal deposition of neuritic plaques, which is a neuropathological landmark in AD (Cummings. N. Engl. J. Med. 2004; 351:56-67). Based on this consideration, this study used the mouse model of AD-type amyloidosis (Hsiao et al. Science 1996; 274:99-102) to test the hypothesis that CR may beneficially influence AD through mechanisms that prevent Aβ generation and eventually, neuritic plaque deposition in the brain.

Material and Methods

Tg2576 Mice and Diets

Three-month-old female Tg2576 mice (Hsiao et al. Science 1992; 274:99-102) (Taconic, Inc. Germantown Inc.) were randomly assigned to a CR or an ad-libitum (AL) dietary regimen. CR was achieved by feeding Tg2576 mice 70% of the calories consumed by the pair-controlled AL animals, as previously reported (Anson et al. Proc. Natl. Acad. Sci. USA. 2003; 100:6216-6220) with a few modifications. At 10 AM each day, CR mice were provided with a food allotment equal to 70% of the average daily caloric intake in the AL-fed group. Food consumption in the CR-fed group was adjusted weekly, based on the average daily caloric intake among the AL-fed mice. Components of the modified AL and CR diets (AL diet #D03020305, CR diet #D03081901; Research Diet, Inc. New Brunswick, N.J.) are further described in Table 1. Tap water was available to both the CR and AL-fed groups. At 12 months of age, the mice were anesthetized with the general inhalation anesthetic 1-chloro-2,2,2-trifluoroethyl difluoromethyl ether (Baxter Healthcare, Deerfield, Ill.) and sacrificed by decapitation. Brain specimens were harvested and hemi-dissected, with one hemisphere post-fixed in 4% paraformaldehyde (24 hr) for morphological studies (see below). Hippocampus and neocortex were dissected from the opposite hemisphere in each case. Brain samples were then rapidly frozen and pulverized in liquid nitrogen, then stored at −80° C. for subsequent ELISA, immunoprecipitation-mass spectrometry (IP-MS) studies for Aβ peptide assessment, western blot studies and α- and β-secretase activity assays. Ependymal fat-pad was collected and weighted at the time of sacrifice. To assess glucose utilization as an index of CR, glucose tolerance was assessed using an intraperitoneal glucose tolerance test (IGTT), as previously described in Ho et al. (FASEB J. 2004; 18:902-904) two weeks before sacrifice. Briefly, mice were given a single dose of glucose administered intraperitoneally (2 g/kg body weight) postprandially, and blood was collected from a tail vein periodically over a 2-hr period. Blood glucose content was assessed using the OneTouch LifeScan System (LifeScan, Milpitas, Calif.) according to manufacturer's instructions. All animal studies were conducted following protocols approved by the Mount Sinai School of Medicine Institutional Animal Use Committee.

Stereologic Assessment of Alzheimer's Disease-Type Amyloid Burden in Tg2576 Mice Freshly harvested mouse brain hemispheres were immersion-fixed overnight in 4% paraformaldehyde, then sectioned in the coronal plane on a Vibratome at a nominal thickness of 50 μm. Every 20th section was selected from a random start position and processed for thioflavin-S staining as previously described (Vallet et al. Acta Neuropathol. (Berl) 1992; 83:170-178). Sections adjacent to those used for thioflavin-S staining were stained with cresyl violet to clarify the cytoarchitecture. This resulted in two adjacent series of 14 evenly spaced sections each. All stereologic analyses were performed using a Zeiss Axiophot photomicroscope equipped with a Zeiss motorized stage and MSP65 stage controller, a high resolution Zeiss ZVS-47E digital camera, and a Macintosh G3 computer running the custom designed software NeuroZoom (Nimchinsky et al. J. Comp. Neurol. 2000; 416: 112-125). The amyloid burden was estimated using the Cavalieri principle with a small size grid (50×50 μm) for point counting according to the method described by Bussiere et al. (Neuroscience 2002; 112:75-91). This procedure provides an unbiased estimate of the fractional volume of the region of interest occupied by amyloid plaques, and the amyloid burden was calculated in percentage from the neocortical or hippocampal volume itself. The number of amyloid plaques was estimated by systematically counting all the thioflavin-S amyloid plaques present in the series of sections at low magnification (10×). Estimates of plaque volume were obtained using a systematic random sampling procedure at intermediate magnification (40×) as previously described in Bussiere et al. (Neuroscience 2002; 112:75-91).

Aβ ELISA Assay

For quantitative assessment of brain Aβ peptides, frozen pulverized tissue was homogenized in 5.0 M guanidine buffer, diluted (1:10) in phosphate-buffered saline containing 0.05% (v/v) Tween-20 and 1 mM Pefabloc protease inhibitors (Roche Biochemicals, Indianapolis, Ind.) and centrifuged for 20 min at 4° C. Total Aβ1-40 or Aβ1-42 was quantified by sandwich ELISA (BioSource, Camarillo, Calif.) as previously reported (Ho et al. FASEB J. 2004:18; 902-904).

Assessment of Amyloid Precursor Protein (APP) Processing (sAPPα, Full-Length APP, ADAM10, ADAM17, ADAM 9, and BACE1)

For western blot analysis of sAPPa, frozen pulverized tissue was homogenized in 0.5 ml of 20 mM Tris.HCl buffer (2 mM EGTA, 1 mM EDTA, 1 mM benzamide, 1 mM dithiothreitol and 1 mM PMSF. PH 7.4) and centrifuged (100, 000×g for 1 hr). The supernatants were collected and protein content was determined by the Bradford method (Bio-Rad Laboratories, Hercules, Calif.) and boiled. Proteins were resolved electrophoretically by SDS-PAGE and transferred to Immobilon-P transfer membranes (Millipore Corporation, MA) and immunoreacted with 6E10 antibody (1:1,000 dilution, Senetek, St. Louis, Mo.) raised against amino acid residues 1-17 of the Aβ domain of APP, a site that constitutes the C-terminus of the sAPPa peptide sequence. For western blot analysis of full-length APP, ADAMs, and BACE1, frozen pulverized tissue was lysed in RIPA buffer (150 mM NaCl, 1% Nonidet P-40, 0.5% deoxycholic acid, 0.1% SDS, 50 mM Tris, pH 8.0) containing protease inhibitors. Lysates were then centrifuged (10,000×g for 10 min) and supernatants collected. Following this step, protein content determination, electrophoresis and membrane transfer were carried out as described for sAPPa assessment. Monoclonal 22C11 antibody (1:1,000 dilution, Chemicon International, Temecula, Calif.) raised against amino acid residues 60-100 of the amino-terminal epitope of human APP was used to assess total full-length APP. Polyclonal anti-ADAM10 and anti-ADAM9 antibodies (1:500 dilution respectively, Chemicon International, Temecula, Calif.), polyclonal TACE antibody (1:1,000 dilution, Santa Cruz Biotechnology, CA) and polyclonal BACE (M-83) (1:200 dilution, Santa Cruz Biotechnology, CA) were used for detection of the concentrations of ADAM10, ADAM9, TACE (ADAM17) and BACE1, respectively. β-actin immunoreactivity (1:3,000 dilution, Sigma, St. Louis, Mo.) was used to control for selectivity of changes. Immunoreactivities were visualized by fluorescence autoradiography using enhanced chemiluminescence detection (SuperSignal Chemiluminescent detection kit, Pierce, Rockford, Ill.) and quantified densitometrically.

Immunoprecipitation-Mass Spectrometry (IP-MS)

IP-MS analysis of Aβ peptides was performed as previously described (Wang et al. J. Biol. Chem. 1996; 271:31894-31902). Formic acid (5M) extracts were neutralized with 2 M Tris to a final pH of 8.0 in the presence of protease inhibitors as previously described (Wang et al. J. Biol. Chem. 1996; 271:31894-31902). Synthetic Aβ12-28 (20 nM) was added as an internal standard and Aβ peptides were immunoprecipitated with the monoclonal antibody 4G8 and 6E10 (Senetek, St. Louis, Mo.) sequentially using Protein A/G-Plus agarose beads. Aβ peptides were analyzed by matrix-assisted laser desorption/ionization time-of-flight mass spectrometry using a Voyager-DE STR mass spectrometer (Applied Biosystems). Each mass spectrum was averaged from 1000 measurements and calibrated with bovine insulin as an internal calibrant. Relative peak intensities of Aβ peptide to internal standard were used for quantitation.

Secretase Activity Assays

α- and β-secretase activities were assessed using commercially available kits (R&D Systems, Minneapolis, Minn.). Briefly, brain samples were homogenized in supplied buffers. The homogenate was then added to a secretase-specific APP peptide conjugated to the reporter molecules EDANS and DABCYL. In the uncleaved form, the fluorescent emissions from EDANS are quenched by the physical proximity of the DABCYL moiety, which exhibits maximal absorption at the same wavelength (495 nm). Cleavage of the peptide by the secretase physically separates the EDANS and DABCYL, allowing for the release of a fluorescent signal. The level of secretase enzymatic activity is proportional to the fluorometric reaction in the homogenate (R & D Systems).

Statistical Analysis

All values are expressed as means±SEM. Differences among means were analyzed using two-way ANOVA, while differences between means were assessed by two-tailed Student t test as indicated in Results and Discussion. In all analyses, the null hypothesis was rejected at the 0.05 level, calculated by the Prism Stat software program (GraphPad Software, Inc., San Diego, Calif.).

Results and Discussion

Chronic Treatment of Tg2576 Mice with a Caloric Restriction Dietary Regimen Resulted in Significantly Lower AD Amyloid Neuropathology in the Brain.

To test the hypothesis that CR can modulate amyloidosis, 3-month-old Tg2576 mice, which develop AD-type amyloid neuropathology by 8 to 10 months of age (Hsiao et al., Science 1996; 274:99-102; Kawarabayashi et al. J. Neurosci. 2001; 21:372-381) were maintained for 9 months with a daily low carbohydrate diet resulting in a 30% lower caloric intake compared to that consumed by age- and gender-matched control Tg2576 mice fed ad-libitum (AL) with a standard laboratory rodent diet.

Nutrient composition in the CR diet was adjusted so that CR was achieved by selectively reducing the carbohydrate content of the diet while consumption of protein, fat, cholesterol, vitamins, and minerals was identical to that of AL-fed Tg2576 mice (Table 1).

TABLE 1

Nutrient composition in ad-libitum (AL) and caloric restriction (CR) diets. Animals on the CR diet consumed amounts of proteins, fat, cholesterol, and micronutrients identical to those consumed by those on the AL diet. CR animals, however, consumed 42% less carbohydrates, accounting for a 30% decreases in total caloric intake.

|  | Ad-libitum diet nutrient composition (per 1 g diet) | Caloric restriction diet nutrient composition (per 0.71 g diet) |
| --- | --- | --- |
| Total calories | 3.8 | 2.7 (30% caloric restriction) |
| Protein (g) | 0.19 | 0.20 |
| Carbohydrate (g) | 0.67 | 0.39 |
| Fat (g) | 0.04 | 0.04 |
| Vitamin mix (mg) | 9.48 | 9.48 |
| Mineral mix (mg) | 9.48 | 9.48 |
| Cholesterol (mg) | 0.20 | 0.20 |
| Cellulose (mg) | 47.38 | 47.38 |
| Dicalcium phosphate (mg) | 12.32 | 12.32 |
| Calcium carbonate (mg) | 5.21 | 5.21 |
| Potassium citrate (mg) | 15.64 | 15.64 |
| Choline bitartrate (mg) | 1.90 | 1.90 |

Figure 9:
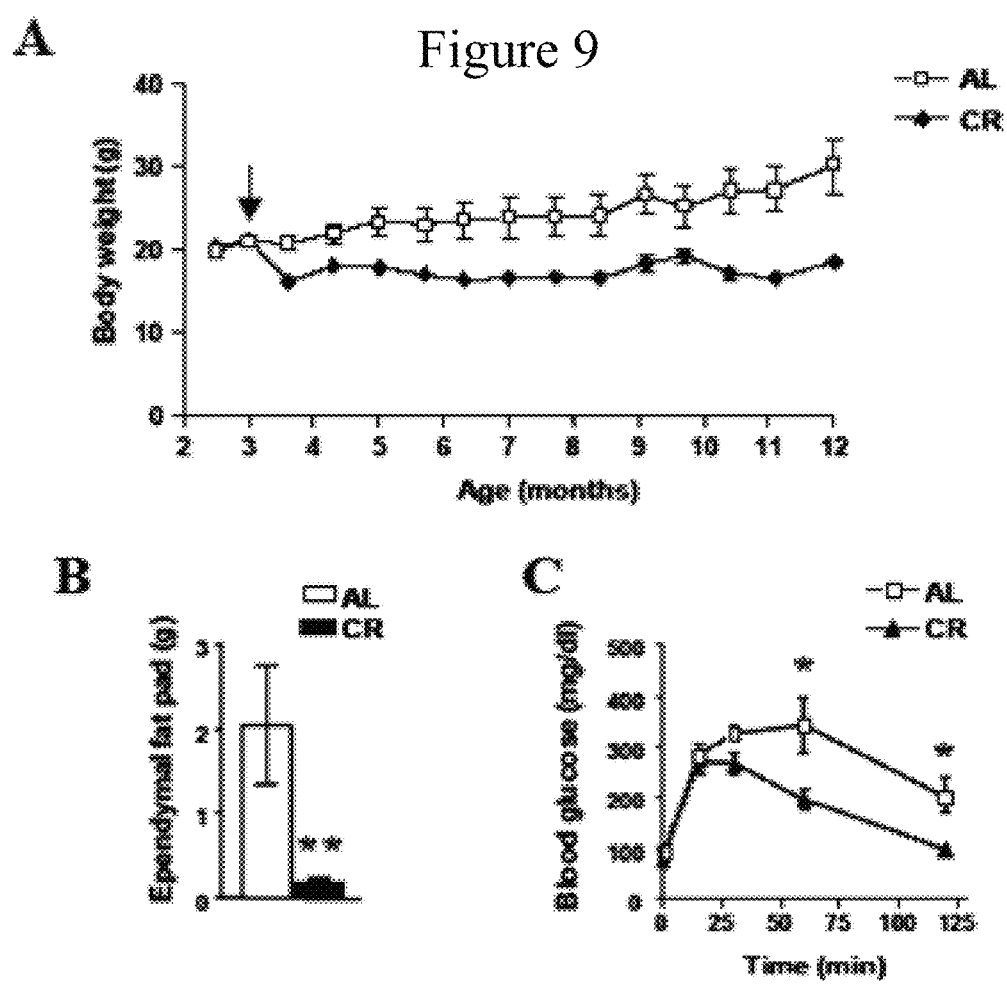
FIG. 9 depicts data showing the change in metabolic indexes in response to low carbohydrate CR dietary regimen relative to AL (ad libitum) feeding. (A) Mean body weight in response to CR versus AL-feeding over time. Arrow indicates initiation of CR treatment regimen. (B) Ependymal fat pad weight assessed at the time of sacrifice. (C) Mean blood glucose content over time in AL and CR mice in response to IGTT. In (A), two-way ANOVA; $p<0.0001$, $F1,139=150.5$, for dietary regimen; $p<0.0249$, $F13,139=2.0$ for time and $p<0.0080$, $F13,139=2.32$ for interaction. In (B), two-tailed t-test, $p<0.02$, AL versus CR. In (C), two-way ANOVA; $P<0.0001$, $F1,50=20.32$ for dietary regimen; $P<0.0001$, $F4,50=30.32$ for glycemic content over time and $P<0.03$, $F4,50=3.02$ for interaction. Values represent mean±SEM, n=5-7 mice per group.

This dietary regimen resulted in body weight stabilization over the 9-month study period among CR Tg2576 mice relative to the AL-fed group (FIG. 9A), and coincided with ~3-fold lower ependymal fat pad weight (FIG. 9B), and improved glucose tolerance response as determined by an intraperitoneal glucose tolerance test (FIG. 9C). These physiological adaptations in the CR Tg2576 mice relative to AL-fed controls are consistent with clinical evidence that low carbohydrate CR considerably improves abnormal glucose control and obesity (Meckling et al. J. Clin. Endocrinol. Metab. 2004; 89:2717-2723; Yancy et al. Ann. Int. Med. 2004; 140:769-777; Stern et al. Ann. Int. Med. 2004; 140:778-785), which are risk factors not only for diabetes but also for AD (Gustafson et al. Arch. Intern. Med. 2003; 163:1524-1528; Vanhanen and Soininen. Curr. Opin. Neurol. 1998; 11:673-677; Kuusisto et al. BMJ 1997; 315:1045-1049).

Figure 10:
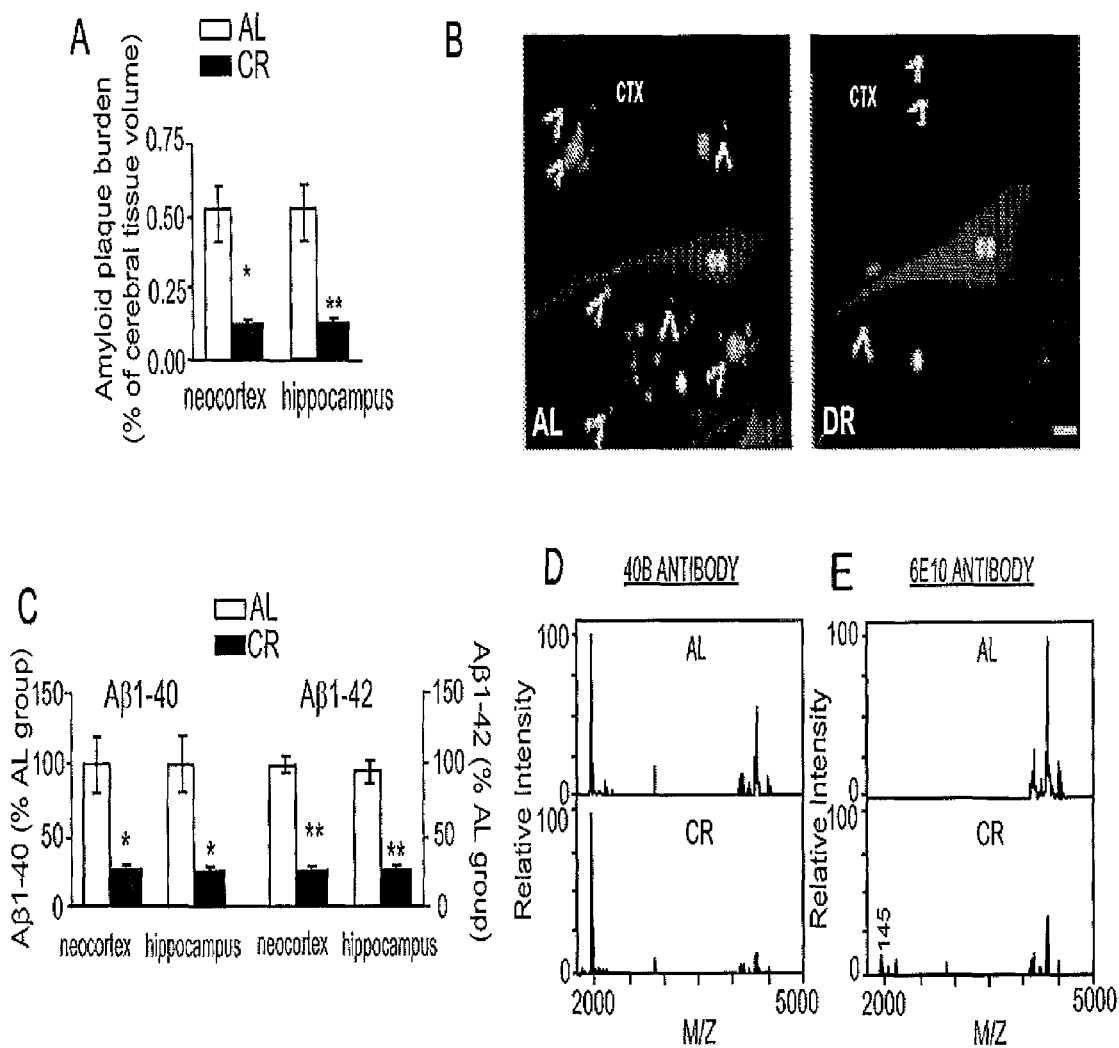
FIG. 10 depicts data showing that CR attenuates AD-type amyloid neuropathology in the brain of Tg2576 mice. Twelve-month-old Tg2576 mice were assessed for indices of AD-type amyloid burden in the neocortex and hippocampus in response to 9 months CR or AL dietary regimens (see Examples). (A) Stereological assessment of neocortical and hippocampal Aβ-amyloid plaque burden (thioflavin-S positive volume as percent of regional volume) (Bussiere et al. Neuroscience 2002; 112:75-91). (B) Representative thioflavin-S positive AD amyloid plaque neuropathology in the neocortex (CTX) and the hippocampal subicular (S) region in the AL (left panel) and CR mice (right panel). (C) Assessment of neocortical and hippocampal Aβ1-40 and Aβ1-42 peptide concentrations in CR and AL-fed control Tg2576 mice. (D-E) IP-MS spectra of neocortical Aβ peptide profiles of CR and AL-fed control mice detected after immunoprecipitation with 4G8 (D) and 6E10 (E) antibodies. The Aβ IP-MS spectra from 4G8 IP was normalized to the internal standard Aβ12-28 while the Aβ IP-MS spectra from 6E10 was plotted using a relative scale to the peak intensity of Aβ1-40 in the AL-fed control group and referenced to their relationship in the 4G8 IP to compare the Aβ fragment peptides. In (D) and (E) MS peaks corresponding to Aβ peptides are indicated with the Aβ peptide sequence number. Peaks labeled as 1-402+ and Insulin2+ represent doubly protonated Aβ1-40 peptide and doubly protonated insulin molecular ions, respectively; Aβ12-28 was added during the IP procedure and used as internal standard (int. std.) ions as previously reported (Wang et al. J. Biol. Chem. 1996; 271:31894-31902). Bar graphs represent group mean+SEM, n=5-7 animals per group; *$p<0.01$, **$p<0.005$, 2-tailed t-test, CR versus AL groups. In (B), arrowheads point toward thioflavin-S positive Aβ amyloid plaques; length bar=30 μM. Abbreviations: CR, caloric restriction; AL, ad-libitum; in (B), CTX, neocortex; S, subiculum; CC corpus collosum.
Figure 11:
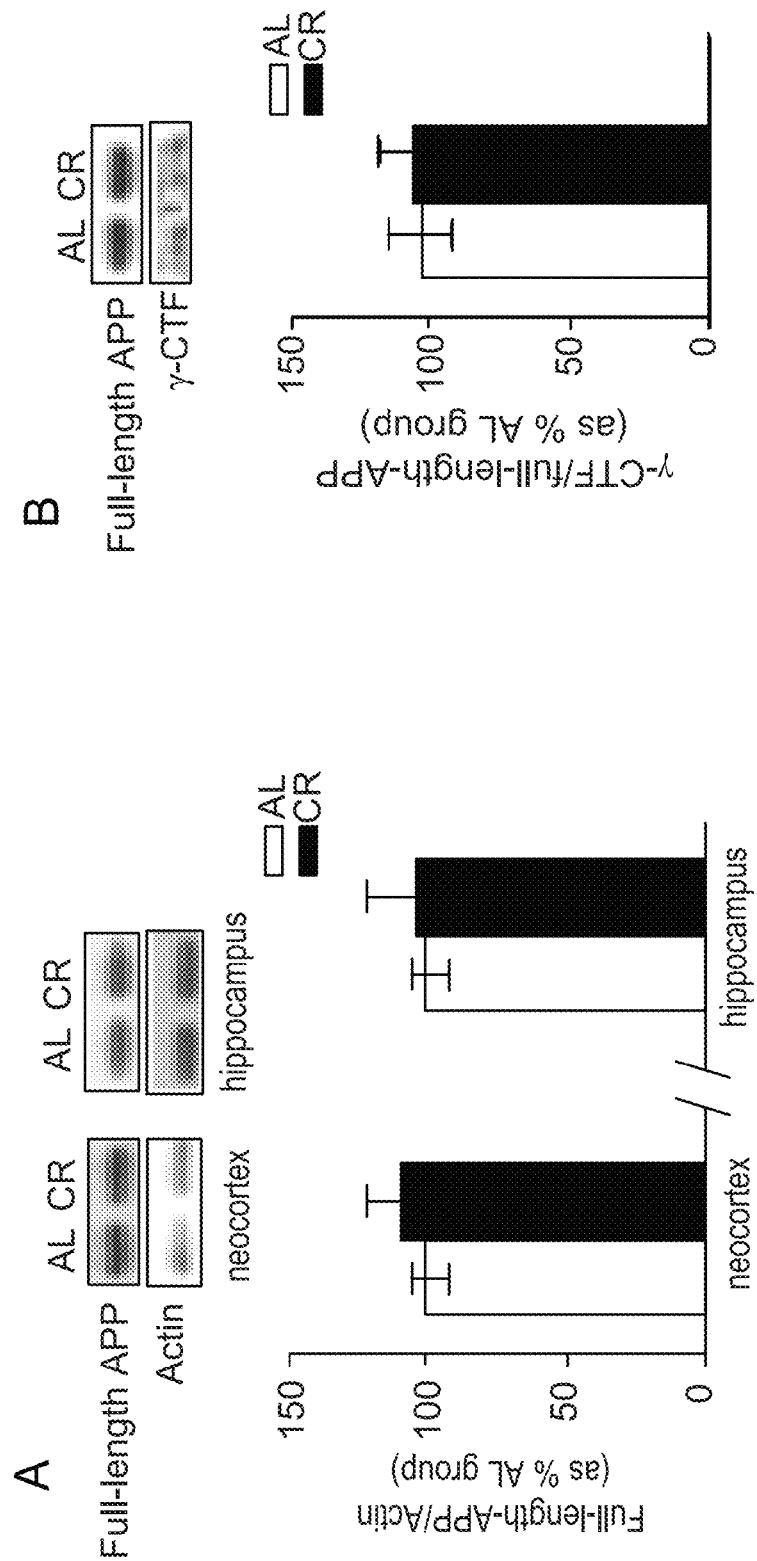
FIG. 11 depicts data showing that there is no detectable change in total full length-APP and CTF-γ concentrations in the brain of Tg2576 mice in response to CR relative to AL-feeding. (A) Assessment of steady state total full-length APP concentrations in neocortical and hippocampal samples relative to β-actin immunoreactive signal; in (A) inset, representative immunoblot of full-length APP and β-actin immunoreactivities. (B) Assessment of APP CTF-γ cleavage product concentrations; in (B) inset, representative CTF-γ and full-length APP immunoreactive signal from the same immunoblot. Bar graph represents group mean+SEM, n=5-7 mice per group.

When Tg2576 mice were examined for AD-type neuropathology at 12 months of age, we found that 9-month CR treatment almost completely prevented cortical and hippocampal AD-type amyloid plaque development (FIGS. 10A-B) relative to animals in the AL-fed group. To further evaluate the anti-amyloidogenic role of CR in the brain of Tg2576 mice, studies were carried out to explore APP processing and Aβ peptide generation using immunoprecipitation (IP)-mass spectrometry (IP-MS) (Wang et al. J. Biol. Chem. 1996; 271:31894-31902). Consistent with the aforementioned ELISA evidence, using 4G8 antibody for Aβ IP, the results confirmed decreased levels of $A\beta_{1-40}$ and $A\beta_{1-42}$ in the same neocortical samples used for the Aβ ELISA assay (FIGS. 10C-D). In addition, a relative proportional reduction in $A\beta_{1-37}$, $A\beta_{1-38}$, and $A\beta_{1-39}$ peptide content was also observed in the neocortex of the CR group compared to the AL-fed control group. This evidence, together with our observation that the concentration of the ~7 kDa carboxy terminal fragment (CTF)-γ cleavage product of APP, an index of γ-secretase activity, was unchanged in the neocortex of the CR group relative to AL-fed controls (FIGS. 11A-B), is consistent with the possibility that γ-secretase activity was not involved in the CR-associated anti-amyloidogenic activity.

The Anti-Amyloidogenic Role of CR is Associated with Selective Promotion of Anti-Amyloidogenic α-Secretase Activity.

To further identify Aβ carboxy-termini peptide fragments that would have been otherwise undetected in the 4G8 IP-MS studies, additional AD IP-MS studies were carried out using 6E10 antibody. Consistent with the 4G8 IP-MS spectra, the results showed decreased levels of Aβ1-40 and Aβ1-42 as well as Aβ1-37, Aβ1-38, and Aβ1-39 peptides, in the CR group relative to AL-fed control animals (FIG. 10E). In addition, the results reveal major elevation in Aβ1-16 peptide fragment concentration in the neocortex of the CR group that was not detected in the AL-fed controls (FIG. 10E). Because α-secretase can cleave APP, eventually resulting in the generation of Aβ C-termini fragments ending at the AA residue leucine16 of Aβ (Lammich et al. Proc. Natl. Acad. Sci. USA 1999; 96:3922-3927; Lichtenthaler et al. J. Clin. Invest. 2004; 113:1384-1387; Wang et al. J. Biol. Chem. 1991; 226:16960-16864), further studies were carried out to explore the role of CR in α-secretase activity in the brain.

Figure 12:
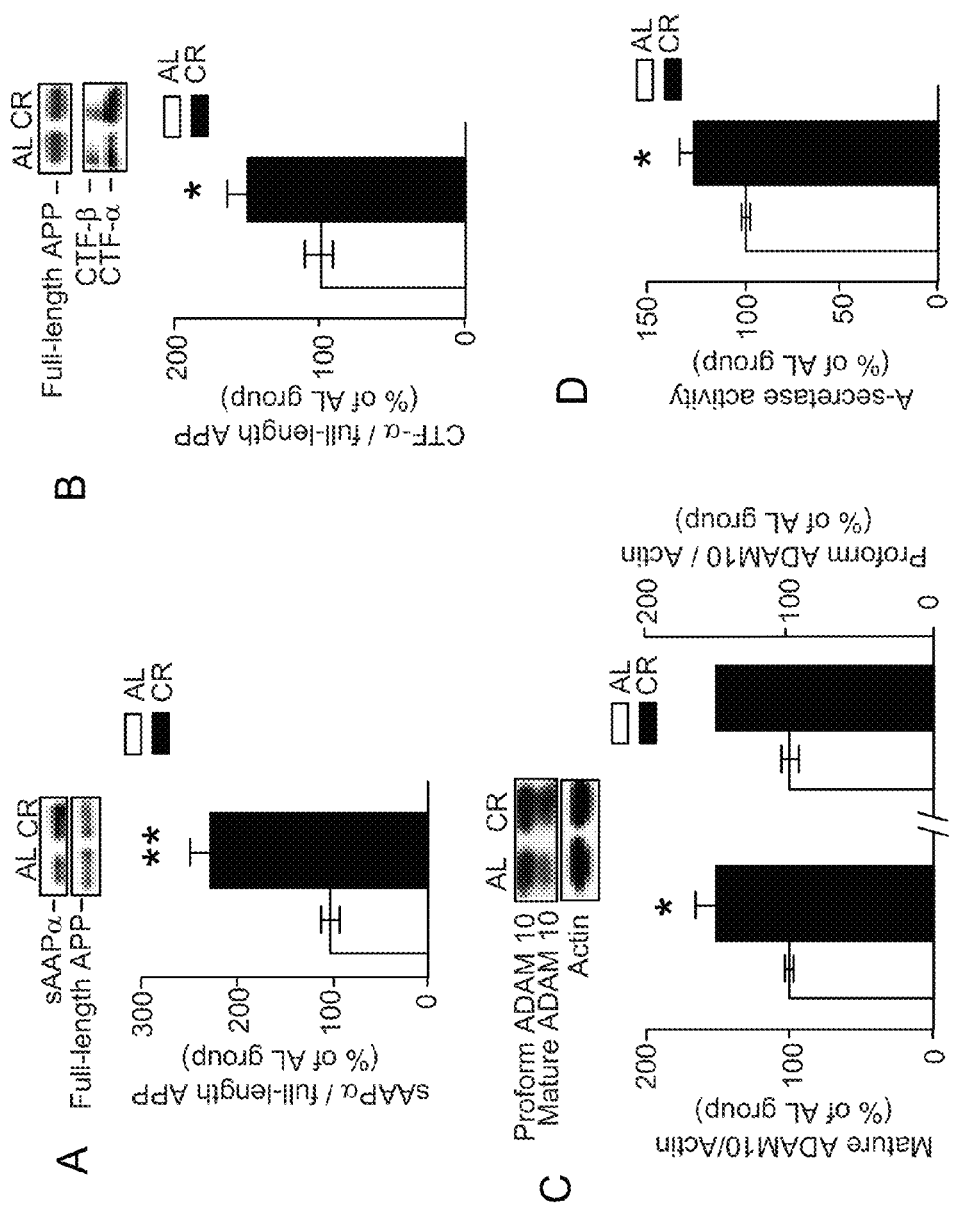
FIG. 12 depicts data showing that CR promotes α-secretase activity in the brain of Tg2576 mice relative to AL-fed control mice. Parallel aliquots of neocortical tissue used for assessment of Aβ peptide concentrations were used in the assessment of indices of α-secretase activity in response to CR, relative to AL feeding. (A) Assessment of changes in neocortical sAPPa concentration expressed as percent of full-length APP immunoreactivity; in (A) inset, representative sAPPa and full-length APP immunoreactive signal in the same sample. (B) Assessment of APP CTF-α cleavage product concentrations; in (B) inset, representative CTF-α (and CTF-β) and full-length APP immunoreactive signal from the same immunoblot. In (C), assessment of mature and proform ADAM10 concentrations in the same neocortical specimen relative to β-actin immunoreactive signal; in (C) inset, representative immunoblot of proform and mature forms of ADAM10 protein species and β-actin immunoreactivities. In (D), fluorometric assessment of α-secretase activity. Bar graphs represent group mean+SEM, n=5-7 mice per group; *$p<0.02$, **$p<0.01$, two-tailed t-test, AL versus CR group.

Cleavage of APP by α-secretase releases the amino-terminal extracellular domain known as soluble α-secretase amyloid precursor protein (sAPPα) domain coinciding with elevation in membrane-bound α-secretase-cleaved APP carboxy-terminal fragment (CTF)-α (Wang et al. J. Biol. Chem. 1996; 271:31894-31902). Studies were therefore carried out to explore the regulation of sAPPα and CTF-α cleavage products of APP in the brain as indices of α-secretase activity in response to CR. Interestingly, CR in Tg2576 mice resulted in a >2-fold elevation in concentration of neocortical sAPPα (FIG. 12A) and membrane-associated CTF-α (FIG. 12B) relative to AL-fed control Tg2576 mice. The increase in CTF-α was somewhat less (~4.6-fold) presumably because of further cleavage of CTF-α by γ-secretase. Compared with the CTF-α fragment, the abundance of CTF-β signal was at the limit of detection in the neocortex of both CR and AL-fed Tg2576 mice, preventing exact quantification (FIG. 12B).

CR May Influence α-Secretase Activity in the Brain, in Part by Selectively Promoting the Generation of Mature, Catalytically Active Adam Species.

In light of recent evidence indicating that the proteinase ADAM10 (a disintegrin and metalloproteinase) may act as an α-secretase (Postina et al. J. Clin. Invest. 2004; 113:1456-1464), further studies were carried out to explore the regulation of ADAM10 expression in the brains of Tg2576 mice in response to CR, relative to AL-fed controls. Both mature (62 kDa) and proform (90 kDa) ADAM10 species were detected in the neocortex of the AL-fed control animals, confirming previous evidence (Postina et al. J. Clin. Invest. 2004; 113: 1456-1464) (FIG. 12C). The 62 kDa mature ADAM10 protein species is known to act as an α-secretase in vitro and to cleave Aβ-derived peptides at leucine$_{16}$ (Lichtenthaler et al. J. Clin. Invest. 2004; 113:1384-1387). Strikingly, CR diet regimen resulted in a 30% elevation of neocortical mature ADAM10 species concentration (FIG. 12C), coinciding with a commensurate elevation in neocortical α-secretase activity (assessed fluorimetrically (Burns et al. J. Neurosci. 2003; 23:5645-5649)) compared to AL-fed control mice (FIG. 12D). No detectable change in proform ADAM10 species concentration was noted in the neocortex of the CR group relative to the AL-fed control group (FIG. 12C). In addition to ADAM10, two other members of the ADAM proteinase family, namely ADAM17 (TACE) and ADAM9, can act as α-secretase in various cell lines (20; 25-27).

Figure 13:
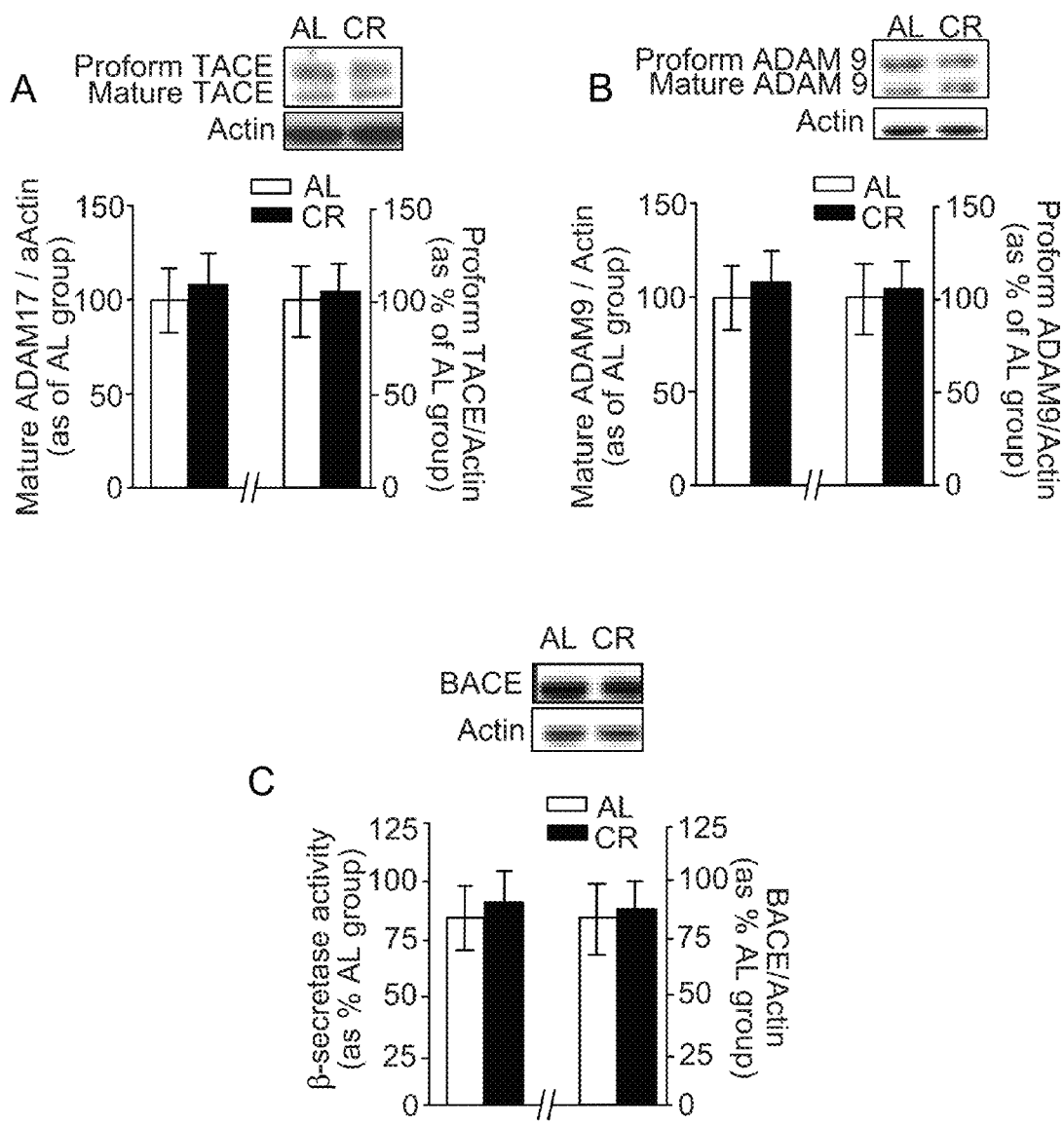
FIG. 13 depicts data showing that there are no detectable changes in neocortical ADAM17 (TACE), ADAM9, BACE, and β-secretase activity in response to CR relative to AL-feeding. (A-C) assessment of proform and mature ADAM17 (TACE), ADAM9, and BACE1 concentrations, relative to β-actin immunoreactive signal, respectively. In (A-C) insets, representative ADAM17, ADAM9, and BACE1 immunoreactivities and β-actin immunoreactive signal in the same sample. In (C), β-secretase was assessed fluorometrically in the parallel neocortical frozen tissue samples used to assess BACE immunoreactive material. Bar graphs represent means+SEM, n=5-7 mice per group.

In parallel studies, CR regimen in Tg2576 mice did not change the concentration of the proform or the mature form of either the ADAM17 (FIG. 13A) or the ADAM9 (FIG. 13B) species, relative to AL-fed control Tg2576 mice. Similarly, there was no detectable change in the neocortical concentration of the BACE1 species or of β-secretase activity in response to CR relative to the AL-fed control group (FIG. 13C).

These studies support the hypothesis that low carbohydrate CR may prevent AD-type amyloid neuropathology through mechanisms that influence α-secretase activity in the brain, possibly by promoting the generation of mature, catalytically active ADAM10 species. Since α-secretase proteolysis of the APP sequence within the Aβ peptide would preclude the generation of amyloidogenic Aβ peptides, the studies here suggest that CR may provide an attractive anti-amyloidogenic strategy by promoting α-secretase activity in the brain. Moreover, because AD-type amyloid neuropathology is undetectable in the brain of 3-month-old Tg2576 mice (Kawarabayashi et al. J. Neurosci. 2001; 21:372-381), the age when our mice were initially exposed to the CR dietary regimen, the studies here support the possibility that CR, by promoting α-secretase activity preventively, possibly through mechanisms involving ADAM10 maturation, may result in reduced AD-type amyloid neuropathology. This possibility is supported by recent evidence showing that decreased α-secretase activity in the brain of dominant negative ADAM10-APP(v717) double transgenic mice develop more amyloid neuropathology than controls (Postina et al. J. Clin. Invest. 2004; 113:1456-1464).

Among the three ADAM family members exhibiting α-secretase activity, ADAM10 has many properties of a physiologically relevant α-secretase: it cleaves APP-derived peptides at the main α-secretase cleavage site between position 16 and 17 of the Aβ region and exhibits α-secretase activity in cultured cells (Lammich et al. Proc. Natl. Acad. Sci. USA 1999; 96:3922-3927). Moreover, the mature ADAM10 species may also act as an efficient α-secretase in the brain of ADAM10-APP$_{(v717)}$ double transgenic mice (Postina et al. J. Clin. Invest. 2004; 113:1456-1464). Our evidence therefore indicates increased brain repair activities as a consequence of sAPPα neurotrophic function.

Current strategies to treat AD are aimed at preventing formation of amyloidogenic Aβ peptides. Therefore, β- and γ-secretases that generate Aβ peptides by sequential cleavage of the amyloid precursor protein (APP) or proteases responsible for degrading released Aβ peptides are obvious and central targets for development of therapeutic reagents (Cummings. N. Engl. J. Med. 2004; 351:56-67). It has, however, been difficult to find safe, selective β- and γ-secretase inhibitors, mainly because of the influence of these inhibitors on other cellular substrates (Cummings. N. Engl. J. Med. 2004; 351:56-67). Thus, the evidence provided here showing that CR may positively influence α-secretase, possibly through mechanisms that may involve the generation of mature, catalytically active ADAM10 species in the brain, provides a basis of potential novel preventative measures aimed at delaying the onset of AD neuropathology. It is also possible, however, that CR might also influence other mechanisms, eventually resulting in decreased amyloid deposition in the brain by promoting α-site cleavage of APP by other proteases (e.g. plasmin (Ledesma et al. EMBO Rep. 2003; 4:1190-1196)) or degradation of released A. In addition, since α-secretase cleavage of APP releases sAPPα, which is well known for its neuroprotective properties (Lichtenthaler et al. J. Clin. Invest. 2004; 113:1384-1387), the results here suggest that promoting low carbohydrate CR dietary regimen may also result in increased brain repair activities as a consequence of sAPPα neurotrophic function.

In conclusion, consistent with the evidence that caloric intake may be a risk factor for AD (Luchsinger. Arch. Neurol. 2002; 59:1258-1263; Hendrie et al. JAMA 2001; 285:739-747; Mattson et al. Physiol. Rev. 2002; 82:637-672; Mattson. Nature 2004; 430:631-639), this study for the first time offers a rational basis for a potential future preventative measure aimed at delaying the onset of AD amyloid neuropathology via control of dietary intake.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A method of treating an individual identified as being at risk of developing Alzheimer's disease comprising providing said identified individual with D-pinitol in an amount and for a sufficient period of time, to reduce the likelihood that said identified individual will develop said Alzheimer's disease, wherein said individual has been identified as being at risk of developing Alzheimer's disease due to a genetic factor, family history, or the presence of mild cognitive impairment.

2. The method of claim 1 wherein said individual has been identified as being at risk of developing Alzheimer's disease due to the presence of at least one ϵ4 allele or the absence of an ϵ2 allele at the apolipoprotein E locus.

3. The method of claim 1 wherein said identified individual is provided with D-pinitol in an amount and for a sufficient period of time to achieve a concentration of D-pinitol in blood or plasma of about 1 to 19 μM.

4. The method of claim 1 wherein said D-pinitol is provided at a daily dose of over 10 mg/kg.

5. The method of claim 1 wherein said individual has been identified as being at risk of developing Alzheimer's disease due to a genetic factor.

6. The method of claim 1 wherein said individual has been identified as being at risk of developing Alzheimer's disease due to family history.

7. The method of claim 1 wherein said individual has been identified as being at risk of developing Alzheimer's disease due to the presence of mild cognitive impairment.

* * * * *